(12) United States Patent
Kuroiwa

(10) Patent No.: US 7,627,208 B2
(45) Date of Patent: Dec. 1, 2009

(54) OPTICAL PROBE AND OPTICAL TOMOGRAPHY APPARATUS

(75) Inventor: Karin Kuroiwa, Ashigarakami-gun (JP)

(73) Assignees: FUJIFILM Corporation, Tokyo (JP); Fujinon Corporation, Saitama-Ken (JP)

( * ) Notice: Subject to any disclaimer, the term of this patent is extended or adjusted under 35 U.S.C. 154(b) by 0 days.

(21) Appl. No.: 12/107,842

(22) Filed: Apr. 23, 2008

(65) Prior Publication Data
US 2008/0260342 A1 Oct. 23, 2008

(30) Foreign Application Priority Data

Apr. 23, 2007 (JP) ............... 2007/112908
Dec. 21, 2007 (JP) ............... 2007/329641

(51) Int. Cl.
*G02B 6/00* (2006.01)
(52) U.S. Cl. .................. 385/31; 600/342; 600/170
(58) Field of Classification Search ............ None
See application file for complete search history.

(56) References Cited

U.S. PATENT DOCUMENTS

| 6,134,003 | A | * | 10/2000 | Tearney et al. | ............ | 356/479 |
| 6,445,939 | B1 | * | 9/2002 | Swanson et al. | ............ | 600/342 |
| 6,477,403 | B1 | * | 11/2002 | Eguchi et al. | ............ | 600/478 |
| 6,498,948 | B1 | * | 12/2002 | Ozawa et al. | ............ | 600/476 |
| 2003/0097044 | A1 | * | 5/2003 | Rovegno | ............ | 600/170 |

FOREIGN PATENT DOCUMENTS

JP 11-056786 A 3/1999
JP 2004-347380 A 12/2004

OTHER PUBLICATIONS

Machine translation of detailed description of JP 11-56786 A, obtained via http://www4.ipdl.inpit.go.jp/Tokujitu/tjsogodben.ipdl?N0000=115 on Aug. 28, 2008.*
Mitsuo Takeda, "Optical Frequency Scanning Interference Microscopes", Optics Engineering Contact, 2003, pp. 426-432, vol. 41, No. 7.

* cited by examiner

*Primary Examiner*—Mike Stahl
(74) *Attorney, Agent, or Firm*—Sughrue Mion, PLLC

(57) ABSTRACT

An elongated probe to be inserted into a tube which is open at a distal end portion of an insertion section of an endoscope includes a sheath constituting the outer circumferential surface of the optical probe, an optical fiber laid in the internal space of the sheath along the longitudinal direction of the sheath, and a deflection scanning means disposed in the internal space of the sheath to deflect light outputted from the optical fiber and is rotated around an axis line extending in the longitudinal direction to scan the deflected light in a circumferential direction of the axis line. A plurality of light transmission sections for transmitting the scanning light is provided, each formed flat on the outer surface, on a side wall of the sheath along the circumferential direction.

12 Claims, 14 Drawing Sheets

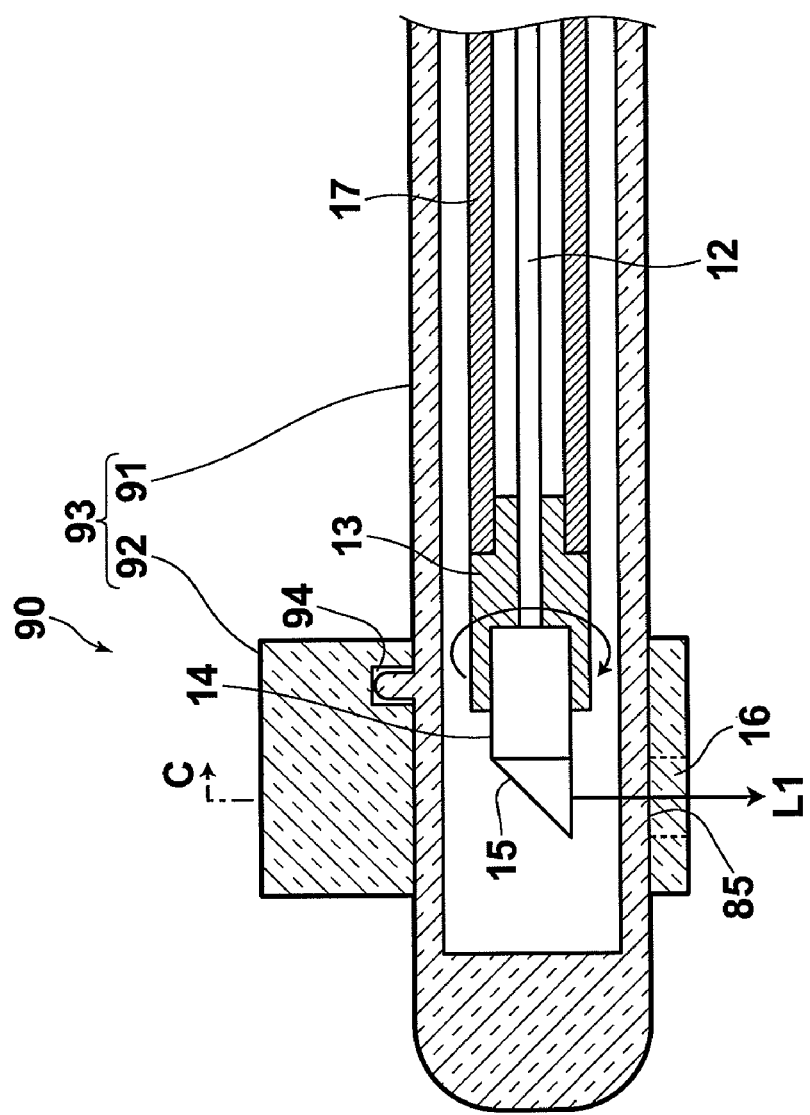
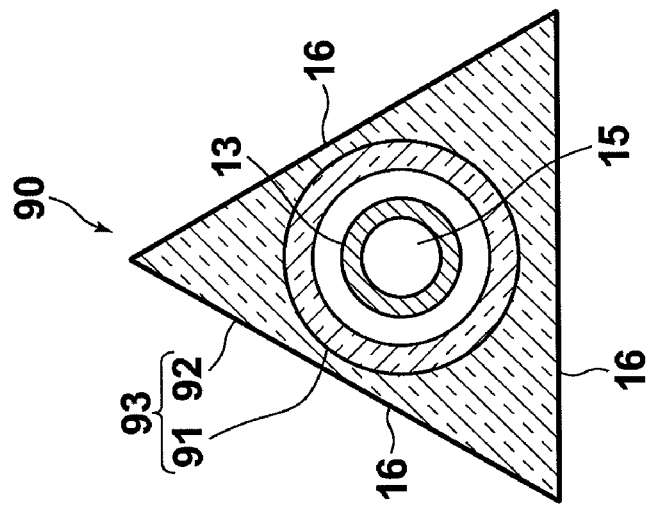
FIG.12B
FIG.12A

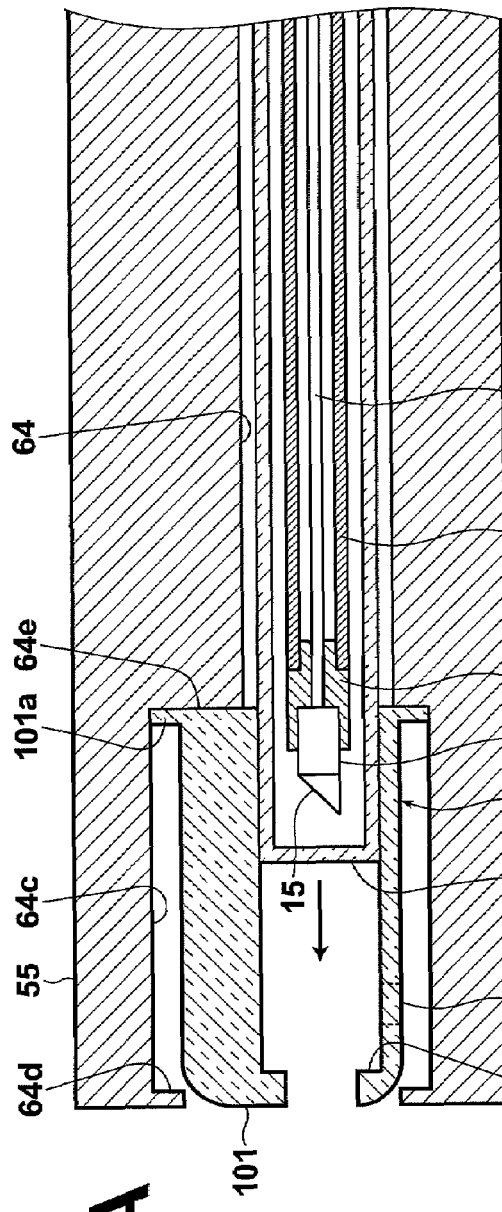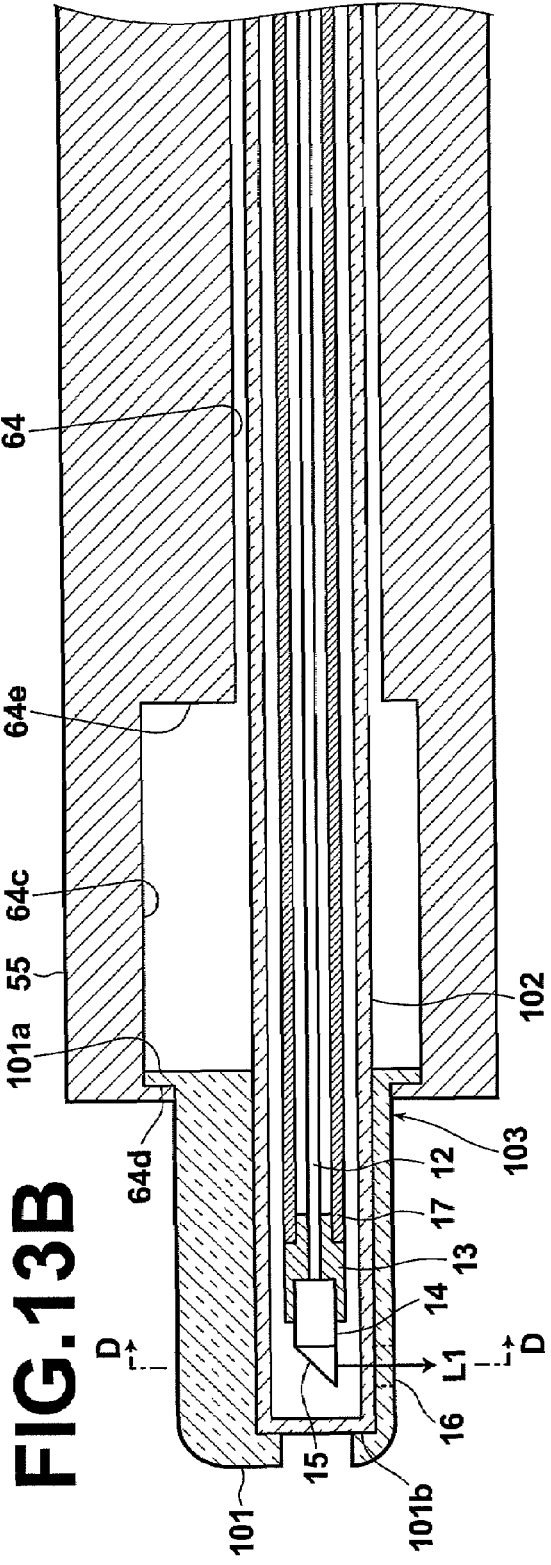

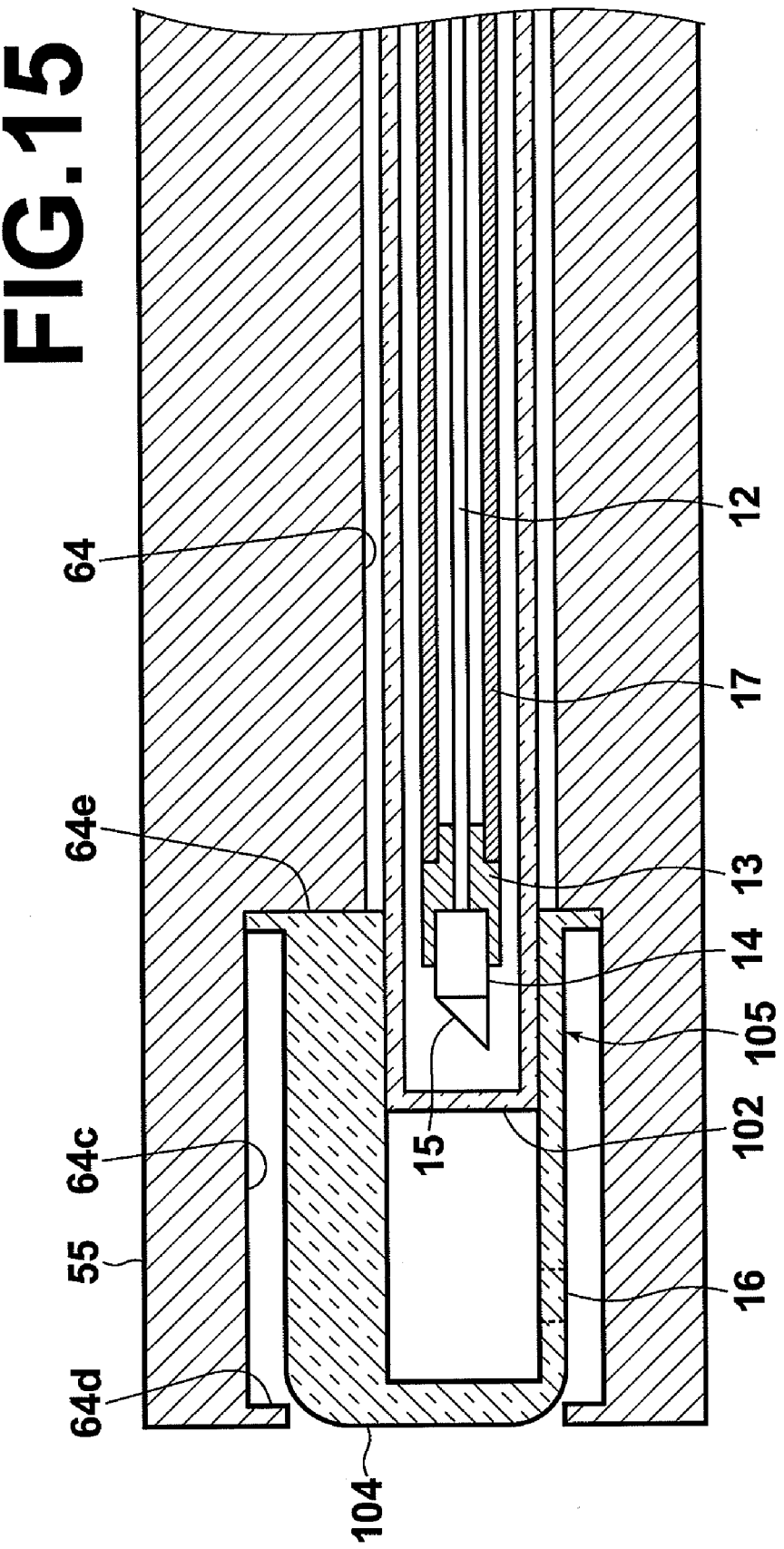

OPTICAL PROBE AND OPTICAL TOMOGRAPHY APPARATUS

BACKGROUND OF THE INVENTION

1. Field of the Invention

The present invention generally relates to an optical probe and an optical tomography apparatus. More specifically, the invention is directed to a probe having an optical scanning function in a circumferential direction with respect to the longitudinal axis of the optical probe, and an optical tomography apparatus for obtaining an optical tomography image of a measuring object by OCT (Optical Coherence Tomography) measurement using the optical probe.

2. Description of the Related Art

As one of the methods for obtaining tomography images of measuring objects, such as living tissues and the like, a method for obtaining a tomography image by OCT measurement is proposed. The OCT measurement is one of the types of optical interference measurement, and a low coherence light outputted from the light source is split into measuring and reference light, and the measuring light is irradiated onto a measuring object, then the reflected light from the measuring object or backscattered light when the measuring light is irradiated thereon is combined with the reference light, and an optical tomography image is obtained based on the intensity of the interference light of the reflected light and the reference light. Hereinafter, reflected light from a measuring object and backscattered light are collectively referred to as the "reflected light".

The OCT measurement is largely grouped into TD-OCT (Time Domain OCT) measurement and FD (Fourier Domain)-OCT measurement. The TD-OCT measurement is a method for obtaining a reflected light intensity distribution corresponding to a position in the depth direction (depth position) of a measuring object by measuring interference light intensity while changing the optical path length of the reference light.

In contrast, the FD-OCT measurement is a method for obtaining a reflected light intensity distribution corresponding to a depth position of a measuring object by measuring interference light intensity with respect to each spectral component of the light without changing the optical path length of the reference light, and performing frequency analysis, typically a Fourier transform, on the obtained spectral interference intensity signals using a computer. The FD-OCT does not require the mechanical scanning used in TD-OCT, so that it has been drawing wide attention as a method that allows high speed measurement.

Typical systems that use FD-OCT measurement are SD-OCT (Spectral Domain OCT) and SS-OCT (Swept Source OCT) systems. The SD-OCT system uses broadband and low coherence light and forms an optical tomography image by splitting interference light into respective frequency components using a spectroscopic device, measuring the intensity of the interference light with respect to each frequency component using an array detector, and performing Fourier transform on the obtained spectral interference signals using a computer.

Generally, each type of optical tomography apparatus described above obtains a tomography image along a certain face of a measuring object. This requires that the measuring light is scanned at least one-dimensional direction on the measuring object. As one of the means for performing such scanning, a dental probe having a measuring window on the side and performing scanning in the depth and horizontal directions by outputting a light beam from the measuring window is known as described, for example, in Japanese Unexamined Patent Publication No. 2004-347380.

In addition, it has been studied to combine each type of the optical tomography apparatus described above with an endoscope for in vivo application, and an optical probe for OCT measurement which is insertable into the forceps channel of an endoscope like that as described in Japanese Unexamined Patent Publication No. 11 (1999)-056786 is known. The optical probe described in Japanese Unexamined Patent Publication No. 11 (1999)-056786 includes an elongated tubular sheath serving as the outer tube of the optical probe, a coil shaft rotatably provided around a longitudinal axis inside the sheath, a rotary drive device for providing rotational power to the coil shaft, and an optical fiber provided inside the coil shaft. The probe is designed to perform optical scanning in a circumferential direction of the sheath by outputting light from the circumferential surface of the sheath.

The combination of the optical tomography apparatus and endoscope described above is useful for obtaining an optical tomography image of a living tissue, and hence development of optical probes for OCT measurement to be inserted into the forceps channels of endoscopes is in progress.

In OCT measurement, a tomography image is obtained based on the signals generated by the reflection light from a measuring object, high intensity reflection light results in high S/N ratio, thereby high quality tomography image may be obtained. If air is present between an optical probe outputting measuring light and a measuring object, however, the reflection light from the measuring object is reduced due to reflection at the interface between the optical probe and the air and interface between the air and the measuring object caused by the difference in the refractive indices thereof. For a measuring object having a water-soluble membrane, such as gastric wall or the like, most of the measuring light is scattered on the surface of the membrane, so that only a small amount of the measuring light reaches the inside of the measuring object, resulting in a degraded S/N ratio. Further, if a liquid, such as water or bodily fluid, is present between the optical probe and the measuring object, the measurement is affected by the light absorption or dispersion by the liquid causing an error. In order to eliminate the problems described above, it is desirable that the optical probe is brought into close contact with the measuring object so that the air or liquid is removed from the gap between the optical probed and measuring object.

In the mean time, the outer tubes of optical probes to be inserted into the forceps channels of endoscopes are commonly formed in a cylindrical shape as described in Japanese Unexamined Patent Publication No. 11 (1999)-056786 due to manufacturing reasons and compatibility with the shapes of the forceps channels. For the cylindrical optical probe with its cross-sectional outer shape being circular, the contact area with a measuring object becomes very small, which gives rise to a problem that a high quality tomography image is obtained only within a narrow area.

It may be conceivable to apply the probe having a measuring window described in Japanese Unexamined Patent Publication No. 2004-347380 to an endoscope probe. In this case, however, the direction of the only one measuring window formed on the side needs to be adjusted so as to appropriately face the measuring object. This will give rise to problems that it requires complicated manipulation, and rapid measurement is prevented.

SUMMARY OF THE INVENTION

The present invention has been developed in view of the circumstances described above, and it is an object of the present invention to provide an optical probe capable of closely contacting a measuring object over a wide range, thereby allowing high quality tomography images to be obtained easily.

A first optical probe of the present invention is an optical probe to be inserted into a tube which is open at a distal end portion of an insertion section of an endoscope, the probe including:

a sheath constituting the outer circumferential surface of the optical probe;

an optical fiber laid in the internal space of the sheath along the longitudinal direction thereof;

a deflection scanning means disposed in the internal space of the sheath to deflect light outputted from the optical fiber, and is rotated around an axis line extending in the longitudinal direction to scan the deflected light in a circumferential direction of the axis line; and a plurality of light transmission sections for transmitting the scanning light, each formed flat on the outer surface, provided on a side wall of the sheath along the circumferential direction.

The term "a tube which is open at a distal end portion of an insertion section of an endoscope" as used herein may be any one of a tube specifically designed for the optical probe of the present invention, a tube so-called "forceps channel" or "treatment tool insertion channel", and a tube provided for other applications.

Further, the term "formed flat on the outer surface" as used herein does not necessarily mean that the outer surface is exactly flat and may be substantially flat.

The first optical probe of the present invention may be formed such that the outer shape of the sheath in cross-section which is perpendicular to the longitudinal direction and including the light transmission sections is a polygon or a polygon with rounded corners.

The first optical probe of the present invention is formed such that the outer shape of the sheath in the cross-section described above becomes a polygon in order to ensure a large contact area in comparison with a conventional optical probe having a circular outer shape. Preferably, the number of corners of the polygon is about three to six. Further, the polygon is not necessarily an equilateral polygon, but an equilateral polygon is preferable from the viewpoint of manufacturing.

A second optical probe of the present invention is an optical probe to be inserted into a tube which is open at a distal end portion of an insertion section of an endoscope, the probe including:

a sheath constituting the outer circumferential surface of the optical probe; an optical fiber laid in the internal space of the sheath along the longitudinal direction thereof;

a deflection scanning means disposed in the internal space of the sheath to deflect light outputted from the optical fiber, and is rotated around an axis line extending in the longitudinal direction to scan the deflected light in a circumferential direction of the axis line; and a plurality of light transmission sections provided on a side wall of the sheath along the circumferential direction and transmits the scanning light, wherein the outer shape of the sheath in cross-section which is perpendicular to the longitudinal direction and including the light transmission sections is substantially an ellipsoid.

The term ellipsoid in "substantially an ellipsoid" as used herein does not necessarily means a mathematical ellipsoid including a circle, but means a shape having a gentler curve than a circle. Preferably the "light transmission sections" in the second optical probe of the present invention are provided on the curved surface sides opposite to the long axis of "substantially an ellipsoid", and not on the curved surface sides opposite to the short axis thereof.

In the first and second optical probes of the present invention, the inner shape of the sheath in cross-section which is perpendicular to the longitudinal direction and including the light transmission sections may be formed in a circle with respect to a point on the axis line.

Further, in the first and second optical probes of the present invention, the sheath may be formed of a first member having a cylindrical shape and a second member which is removably attachable to the first member and on which the plurality of light transmission sections is provided along the circumferential direction.

In this case, the tip of the cylindrical first member is closed or open. Further, in the area where the light transmission section overlaps with the first member, the first member has an optical transparency.

The second member may be a cap member that covers a distal end portion of the first member or a strip-like member that covers a portion of the circumferential surface of the first member.

Further, the second member may be a cover member having an inner diameter that allows insertion of a distal end portion of the first member and stored inside of the tube of the insertion section of the endoscope, the cover member being slidable in the longitudinal direction of the tube, and the sheath may be configured such that the cover member protrudes from the insertion section while covering the distal end portion of the first member when the first member is moved in the tip direction of the tube and allows the light to be outputted through one of the light transmission sections.

The tip of the cover member may be closed or open.

An optical tomography apparatus of the present invention is an apparatus constituted by any one of the optical tomography apparatuses employing various different types of measuring systems described above and one of the optical probes of the present invention. More specifically, the apparatus including:

a light source that emits light;

a light splitting means that splits light emitted from the light source into measuring light and reference light;

an irradiation optical system that irradiates the measuring light on a measuring object;

a light combining means that combines reflection light from the measuring object when the measuring light is irradiated thereon with the reference light;

an interference light detection means that detects interference light of the combined reflection and reference light; and an image obtaining means that detects an intensity of reflection light from each of a plurality of depth positions of the measuring object based on the frequency and intensity of the detected interference light, and obtains a tomography image of the measuring object based on the intensity of the reflection light from each of the depth positions, wherein the irradiation optical system includes an optical probe of the present invention.

According to the first optical probe of the present invention, light is scanned in a circumferential direction by the deflection scanning means, and the light transmission sections for transmitting the scanning light and having flat outer surfaces are provided on a side wall of the sheath serving as the circumferential wall of the optical probe. Consequently, when the optical probe is brought into close contact with a measuring object, a large contact area is ensured in comparison with a conventional optical probed having a cylindrical sheath, so that high quality tomography images may be obtained over a wide range. Further, a plurality of light transmission sections is provided along the circumferential direction, so that it is easy to set one of the light transmission sections to face the measuring region of a measuring object.

According to the second optical probe of the present invention, light is scanned in a circumferential direction by the deflection scanning means, and light transmission sections for transmitting the scanning light are provided on a side wall of the sheath serving as the circumferential wall of the optical probe, in which the outer shape of the sheath is formed substantially an ellipsoid in cross-section which is perpendicular to the longitudinal direction and including the light transmission sections, thereby the probe may have a gentler curve than a circle. Consequently, when the optical probe is brought into close contact with a measuring object, a large contact area is ensured in comparison with a conventional optical probed having a cylindrical sheath, so that high quality tomography images may be obtained over a wide range. Further, a plurality of light transmission sections is provided along the circumferential direction, so that it is easy to set one of the light transmission sections to face the measuring region of a measuring object.

In the optical probes of the present invention, when the sheath is formed of a cylindrical first member, and a second member which is removably attachable to the first member and on which the plurality of light transmission sections is provided along the circumferential direction, cleaning of the members and replacement of a deteriorated member become easy. Further, even if the second member becomes a particular shape, only a small portion having the light transmission sections may be formed by the second member, and the major portion of the sheath may be formed by the first member having a simple shape, so that the manufacturing becomes easy in comparison with the case in which the sheath is formed of a single part, and the productivity is improved.

According to the optical tomography apparatus of the present invention, the irradiation optical system includes one of the optical probes of the present invention, so that it is easy to obtain high quality tomography images over a wide range.

BRIEF DESCRIPTION OF THE DRAWINGS

FIG. 12A is a cross-sectional view taken along the line C-C in FIG. 12B.

FIG. 12B is a schematic side cross-sectional view of an optical probe according to a third embodiment of the present invention.

FIGS. 13A and 13B are schematic side cross-sectional views of an optical probed according to a fourth embodiment of the present invention.

FIG. 15 is a side cross-sectional view of a modification of the optical probe of the present invention.

DESCRIPTION OF THE PREFERRED EMBODIMENTS

Figure 1A:
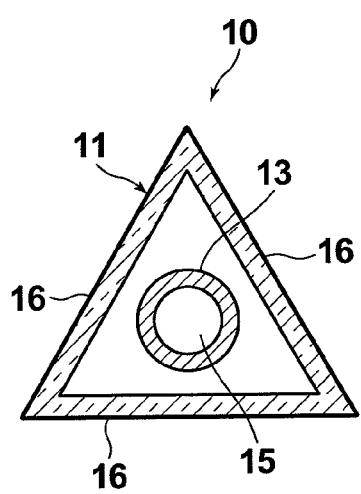
FIG. 1A is a cross-sectional view taken along the line A-A in FIG. 1B.
Figure 1B:
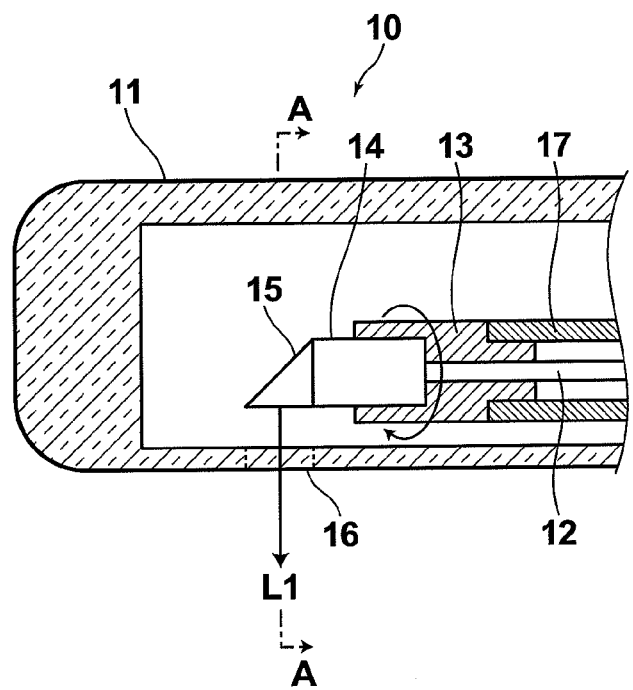
FIG. 1B is a schematic side cross-sectional view of an optical probe according to a first embodiment of the present invention.
Figure 2:
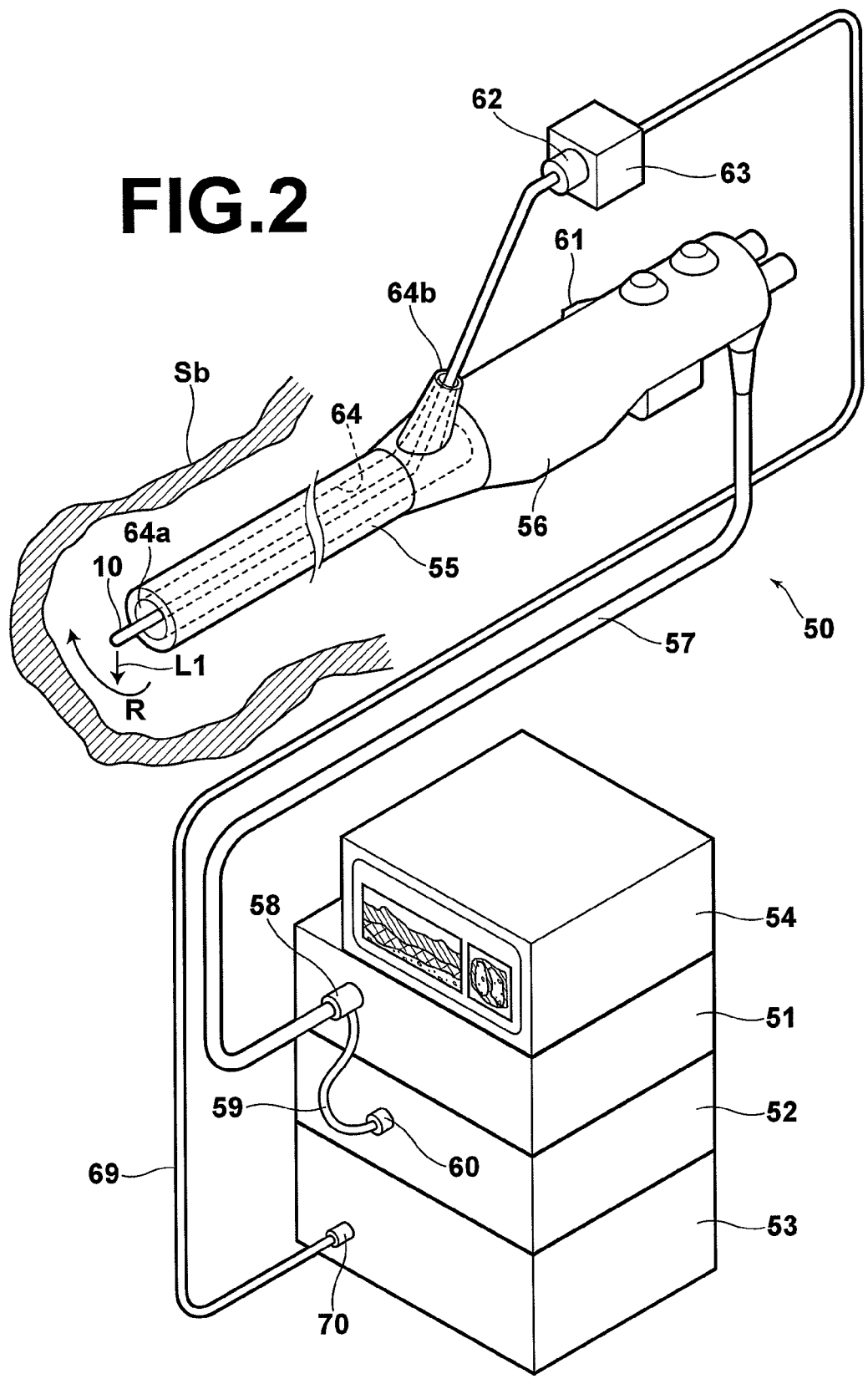
FIG. 2 is an overall perspective view of an optical tomography apparatus to which the optical probe shown in FIGS. 1A and 1B is applied.

Hereinafter, exemplary embodiments of the present invention will be described with reference to the accompanying drawings. FIGS. 1A and 1B are schematic cross-sectional view and schematic side cross-sectional view of an optical probe 10 according to a first embodiment of the present invention respectively. The optical probe 10 is to be inserted into a forceps channel 64 of an endoscope constituting an optical tomography apparatus, the overall configuration of which is illustrated in FIG. 2.

First, the outline of the optical tomography apparatus will be described with reference to FIG. 2. The apparatus includes: an endoscope 50 having an optical probe 10; a light source unit 51 to which the endoscope 50 is connected; a video processor 52; optical tomography processing unit 53; and a monitor 54 connected to the video processor 52. The endoscope 50 includes a flexible elongated insertion section 55, an operation section 56 connected to the proximal end of the insertion section 55, and a universal cord 57 extended from a side section of the operation section 56.

A not shown light guide for transmitting illumination light from the light source unit 51 is inserted into the universal cord 57, and a light source connector 58 which is detachably attachable to the light source unit 51 is provided at an end of the universal cord 57. From the light source connector 58, a signal cable 59 is extended, and a signal connector 60 which is detachably attachable to the video processor 52 is provided at the end section of the signal cable 59. The light source unit 51 is a unit for irradiating illumination light on a portion of a measuring object Sb from which a tomography image is obtained in a manner as will be described later.

The insertion section 55 is to be inserted, for example, into a body cavity of a human body to observe the measuring object, such as an organ or the like. The insertion section 55 has a bendable bent section formed at the distal end thereof, and a bending operation knob 61 for bending the bent section is provided in the operation section 56.

A forceps channel 64 is provided inside the insertion section 55 along the longitudinal direction thereof, which is a tube for inserting the optical probe 10 and a treatment tool, such as forceps or the like. One end of the forceps channel 64 is open at the distal end of the insertion section 55 to form a tip opening 64a, and the other end thereof is branched at the distal side of the operation section 56, one of which becomes a forceps insertion opening 64b above the operation section and the other of which communicates with inside the operation section 56 to the middle of the way.

The distal side of the optical probe 10 formed elongation shape is inserted into the forceps channel 64 from the forceps insertion opening 64b. Then, the optical probe 10 is inserted through the forceps channel 64 to irradiate light on the measuring object Sb by protruding the tip portion thereof from the tip opening 64a. The proximal end of the optical probe 10 is placed outside the endoscope 50 and connected to a controller 63 through a connector 62. An optical fiber 69 is connected to the controller 63, and one end of the optical fiber 69 is optically coupled to the optical probe 10. The other end of the optical fiber 69 is extended outside the endoscope and connected to the optical tomography processing unit 53 through a detachably attachable connector 70.

It is noted that the distal end section of the insertion section 55 of the endoscope 50 further includes an observation window for observing the measuring object Sb, an illumination window for irradiating illumination light, an air/water nozzle for removing debris, and the like, but they are omitted in FIG. 2.

Next, the optical probe 10 will be described with reference to FIGS. 1A and 1B. The optical probe 10 is designed to irradiate measuring light L1 onto a measuring object Sb from a side of the distal side thereof, and constitutes a part of irradiation optical system of an optical tomography apparatus. FIG. 1B is a side cross-sectional view of the distal side of the optical probe 10, and FIG. 1A is a cross-sectional view taken along the line A-A in FIG. 1B.

The optical probe 10 includes: a sheath 11 constituting the outer circumferential face; an optical fiber 12 laid inside of the optical probe 10 along the longitudinal direction thereof; a GRIN lens (gradient index lens) 14 fixed at the tip of the optical fiber 12 by a fixing member 13; and a prism mirror 15 fixed to the GRIN lens 14. The light outputted from the optical fiber 12 is focused by the GRIN lens so that the measuring object Sb is brought into focus, reflected by a reflection surface of the prism mirror 15 such that the optical axis thereof is bent by 90 degrees and deflected to head toward a side of the sheath 11.

The sheath 11 is made of a transparent material that allows light outputted from the optical fiber to pass therethrough, which is also flexible in order not to damage the measuring object Sb when brought into contact therewith. As an example of such material, transparent Teflon® may be used for the sheath 11. Further, it is desirable to select a material having a refraction index which is identical or close to that of the measuring object Sb in order to reduce reflection at the interface between the sheath 11 and measuring object Sb.

The sheath 11 in the present embodiment is formed in an angular tube such that the outer shape in cross-section which is perpendicular to the longitudinal direction of the optical probe 10 becomes an equilateral triangle as shown in FIG. 1A. A light transmission section 16 for transmitting light deflected by the prism mirror 15 is formed, with its outer surface made flat, on each of the three side walls constituting the circumferential wall of the sheath 11. The light transmission section 16 is the portion between the two dashed lines in FIG. 1B.

The portion of the sheath 11 other than the light transmission section 16 is not necessarily formed identical to the light transmission section 16. But from the manufacturing point of view, it is easier to form sheath 11 in the same shape using the same material over the longitudinal direction thereof and to use a portion thereof as the light transmission section 16.

A flexible shaft 17 is fixed by a fixing member 13 around the outer circumference of the optical fiber 12. The flexible shaft 17 may be, for example, a coil shaft having a coiled circumference. The optical fiber 12, GRIN lens 14, prism mirror 15, and flexible shaft 17 are formed so as to be integrally rotatable around the longitudinal axis line of the optical probe 10, more specifically around the optical axis of the optical fiber 12, with respect to the sheath 11, as shown by the arrow in FIG. 1B.

Figure 3:
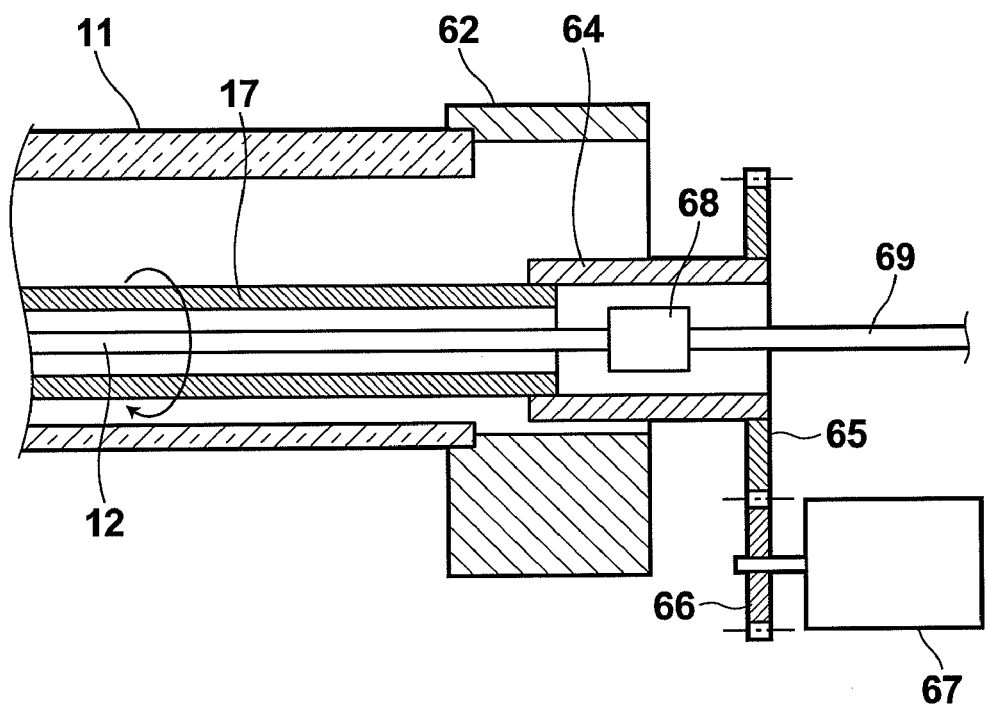
FIG. 3 is a cross-section view of a rotation mechanism of the probe shown in FIGS. 1A and 1B.

Here, a mechanism for rotating the flexible shaft 17 will be described with reference to FIG. 3. The proximal end of the optical probe 11 is connected to a rotation mechanism in the controller 63 through the connector 62. The proximal end of the flexible shaft 17 is connected to the rotation mechanism is connected to the side of the rotation mechanism through the connector 64 and freely rotatable around the optical axis of the optical fiber 12. The flexible shaft 17 is rotated by a shaft rotation motor 67 through a gear wheel 65 fixed around the outer circumference thereof and a gear wheel 66 that engages with the gear wheel 65. The rotation mechanism include a not shown encoder, and the shaft rotation motor 67 rotates the flexible shaft 17 at a predetermined constant speed based on a signal from the rotation encoder.

The proximal end of the optical fiber 12 inside the optical probe 10 is optically coupled to an optical fiber 69 located on the rotation mechanism side through a connector 68. The connector 68 allows rotation of the optical fiber 12 while maintaining the optical coupling, and light from a not shown light source is transferred from the optical fiber 69 to the optical fiber 12.

As the flexible shaft 17 is rotated, the optical fiber 12 and prism mirror 15 shown in FIG. 1B are also rotated. This allows light deflected by the prism mirror 15 to scan in a circumferential direction of the sheath 11, and in this way the prism mirror 15 acts as the deflection scanning means of the present invention. It is noted that the mechanism of rotating the deflection scanning means of the present invention is not limited to this, and other embodiments may also be used.

Figure 4:
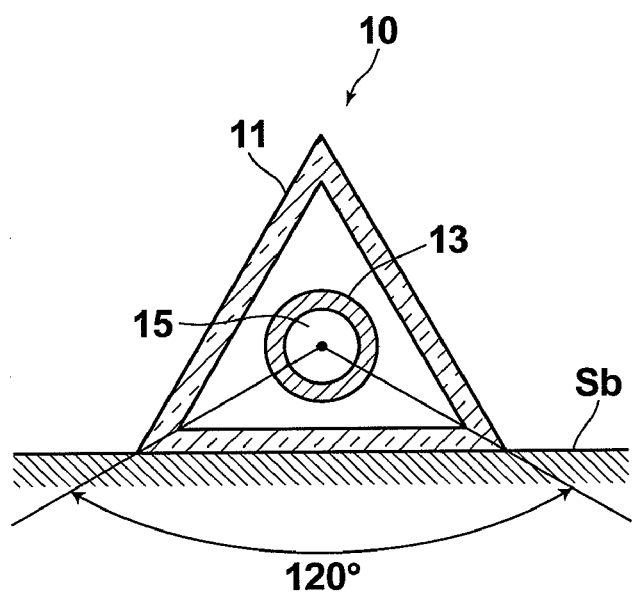
FIG. 4 is a drawing illustrating a state when the optical probe shown in FIGS. 1A and 1B is brought into close contact with a measuring object.

As illustrated in FIG. 4, in the optical probe 11 of the present embodiment, the contact area of one light transmission section 16 is approximately 120 degrees in terms of the angle between the lines connecting the optical axis of the optical fiber 12 and each of the ends of the contact area. That is, one light transmission section 16 allows approximately 120 degrees of viewing angle in the optical scanning in the circumferential direction.

Figure 5:
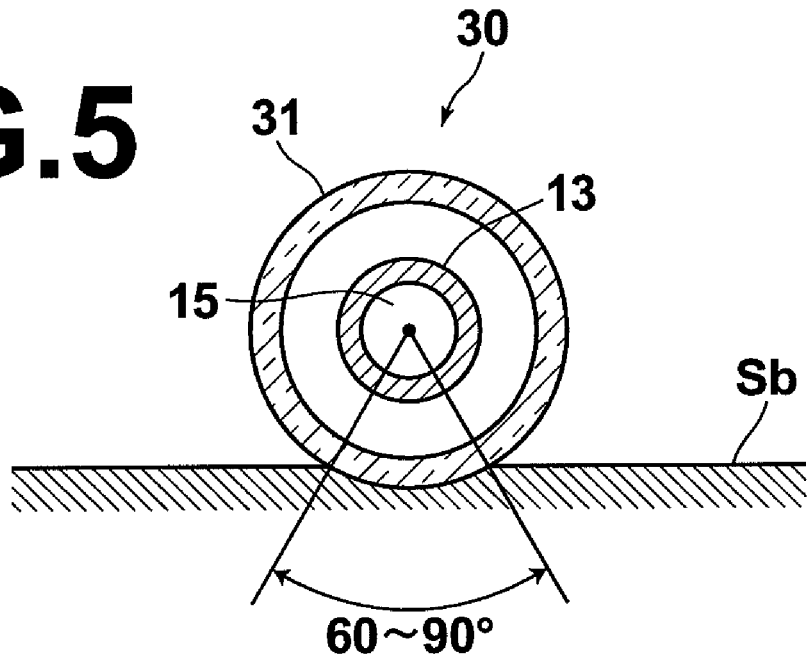
FIG. 5 is a drawing illustrating a state when a conventional optical probe is brought into close contact with a measuring object.

In contrast, as illustrated in FIG. 5, in a conventional general optical probe, the viewing angle is approximately 60 to 90 degrees at most when brought into contact with a measuring object Sb by pressing the optical probe with an ordinary force, since the sheath 31 is formed in a cylindrical shape. The diameter of an ordinary optical probe inserted into the forceps channel of an endoscope is approximately 1 to 2.5 mm, so that the radius of curvature of the surface of an organ in a body cavity is very great in comparison with the radius of curvature of the outer shape of the optical scope and surface can be regarded as almost flat.

As can be seen from FIGS. 4 and 5, according to the optical probe 10 of the present embodiment, a wider contact area with a measuring object Sb is ensured in comparison with an optical probe having a circular cross-section, so that it provides a wider viewing angle and more stable contact with the measuring object Sb.

By bring the optical fiber 10 into close contact with a measuring object Sb, optical loss due to reflection at the interfaces when air is present between them, optical loss due to scattering on the surface of a water-soluble membrane when the membrane is present between them, or optical loss due to light absorption or dispersion when a liquid is present between them is eliminated. Thus, the optical probe 10 allows a high quality tomography image to be obtained over a wide range.

Further, an optical probe having a circular cross-section is likely to produce ghosts due to multiple reflections on the sheath. In contrast, in the sheath 11 having an equilateral triangular cross-sectional shape shown in FIG. 1B, it is almost unlikely that the multiple reflections on the sheath are fed back to the optical fiber 12, so that the ghosts may be reduced.

Furthermore, for the optical probe having only one light transmission section on a side described in Japanese Unexamined Patent Publication No. 2004-347380, it is necessary to rotate the optical probe up to 180 degrees in order to place the light transmission section opposite to a measuring object Sb. In contrast, a probe having an equilateral triangular cross-sectional shape with a light transmission section 16 provided on each of the side walls of the sheath 11, as in the optical probe 10 of the present embodiment, it is only necessary to rotate up to 60 degrees in order to place the light transmission section opposite to a measuring object Sb, allowing ease of adjustment operation.

Here, it is desirable that the optical probe 10 of the present embodiment is provided with an antireflection film on the inside surface of the sheath 11 in order to prevent light deflected by the prism mirror from being reflected on the inside surface of the sheath 11. In this case, the incident angle of the light incident on the sheath differs depending on the incident position on the light transmission section 16, so that it is desirable that an antireflection film having an optimum incident angle distribution that differs depending on the incident position is formed.

Further, dependence of the reflectance on the incident angle is different between P polarization and S polarization so that it is desirable to correct the polarization characteristics by regarding the incident angle of the measuring light L1 at each incident position. For example, the polarization characteristics may be corrected in an optical tomography apparatus to be described later by separating interference light obtained by combining reflection light with reference light into P polarization component and S polarization component and detecting the interference light with respect to each polarization component. This is particularly necessary in the measurement of observing polarization characteristics, such as an optical rotation measurement or the like.

Figure 6:
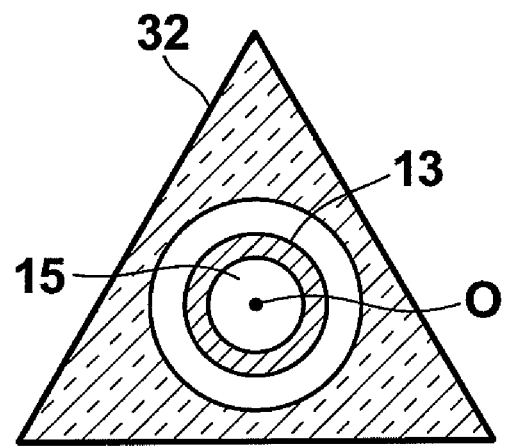
FIG. 6 is a cross-sectional view of a modification of the optical probe of the present invention.

One of the measures to solve the problem of incident angle described above is to form the sheath such that the inner shape thereof in cross-section which is perpendicular to the longitudinal direction thereof and including the light transmission sections becomes a circle with respect to a point on the axis line. FIG. 6 illustrates one such example. The sheath 32 shown in FIG. 6 has a triangular outer shape in the cross-section but has a circular inner shape with respect to a point "O" on the axis line of the optical fiber 12. In the example shown in FIG. 6, the incident angle from the prism mirror to the sheath 32 is invariably 90 degrees, so that it is not necessary to regard incident angle dependence.

The sheath having different shapes between the outer and inner shapes in cross-section, like that shown in FIG. 6, has a thickness which differs from portion to portion. Consequently, the optical path length differs depending on the incident position of the sheath 32, which may possibly cause distortions in an image to be formed. But the distortions in the image may be reduced by regarding and correcting the optical path length difference in the calculation processing performed by an image obtaining means 150 to be described later. The optical path length of light incident on each point of the sheath may be calculated easily from the incident angle, refraction index of the sheath, shape and size of the sheath, and the like.

Further, in the optical probe 10 of the present embodiment, the distance from the light output point of the prism mirror 15 to a measuring object Sb closely contacted with the sheath differs depending on the incident position, so that the focus position of the GRIN lens possibly may not correspond to the measuring object Sb. In such a case, for example, a configuration may be adopted in which the distance between the optical fiber 12 and GRIN lens 14 is made variable, and either one of them is moved in the longitudinal directions by a drive means, such as a piezoelectric actuator or a micro motor, thereby focus position of the GRIN lens may be changed and the measuring object may be brought into focus.

It is noted that the shapes of the optical probe of the present invention are not limited to those shown in FIGS. 1A and 6, and various modifications may be conceivable. For example, the sheath may be formed such that the outer shape thereof in cross-section which is perpendicular to the longitudinal direction thereof is a polygon or a polygon with rounded corners. A polygonal shape with rounded corners is more preferable to a polygonal shape with sharp corners, since it is less likely to damage the measuring object Sb.

Figure 7A:
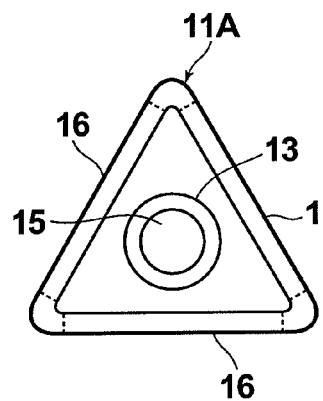
FIGS. 7A to 7F illustrate cross-sectional shapes of modifications of the optical probe of the present invention.
Figure 7B:
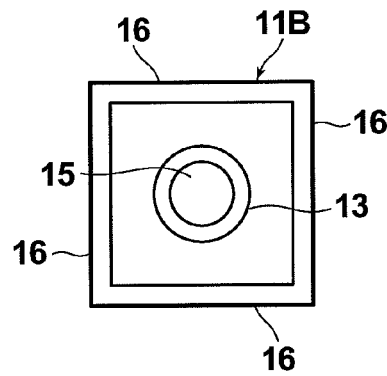
Figure 7C:
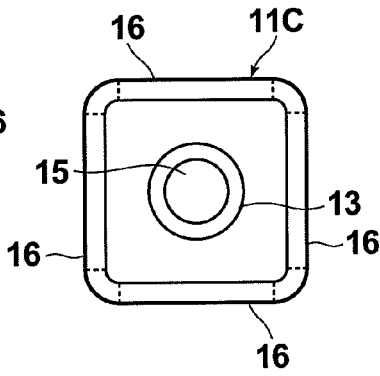
Figure 7D:
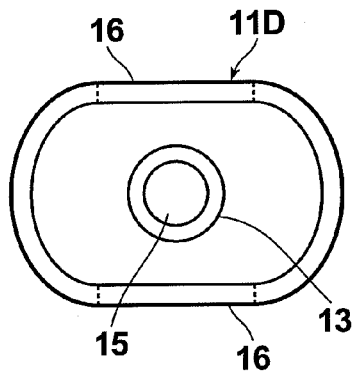

FIGS. 7A to 7F illustrate the shapes of various modifications of the sheath in cross-section which is perpendicular to the longitudinal direction thereof and including the light transmission sections. In FIGS. 7A, 7C, 7D, and 7E, the light transmission sections are the portions between the dashed lines, and in FIGS. 7A to 7E, hatched lines to indicate cross-sections are omitted for clarity. FIG. 7A illustrates a sheath 11A having an equilateral triangular shape with rounded corners. FIG. 7B illustrates a sheath 11B having a square shape. FIG. 7C illustrates a sheath 11C having a square shape with rounded corners. FIG. 7D illustrates a sheath 11D having a shape in which a pair of opposing light transmission sections 16 is connected by a curved line.

Figure 7E:
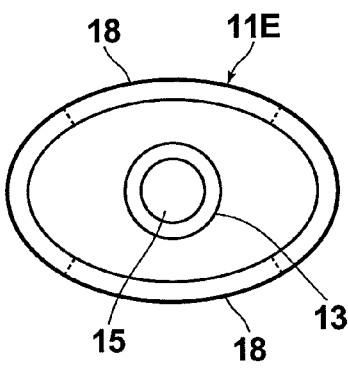

FIG. 7E illustrates a sheath 11E having an elliptical outer shape in cross-section with light transmission sections 18 on the curved surfaces opposite to the long axis of the ellipsoid. In this way, by forming a sheath with a surface having a large curvature in comparison with a conventional general cylindrical sheath and providing a light transmission section on the surface, the contact area may become larger than the conventional sheath, thereby advantageous effects identical to those of the embodiment described above may be obtained.

Figure 7F:
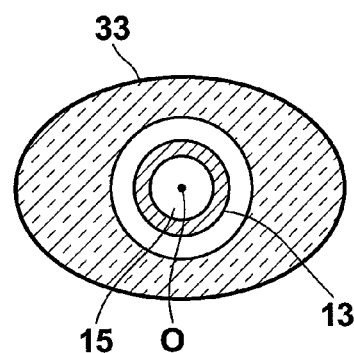

Further, the sheath may be formed so as to have the outer shape like one of those illustrated in FIGS. 7A to 7E with the inner shape to be circular with respect to a point on the axis line as illustrated in FIG. 6. In this case, the problem of incident angle dependence may be solved as described earlier. One such example is shown in FIG. 7F. FIG. 7F illustrates a sheath 33 having an elliptical outer shape with a circular inner shape with respect to a point "O" on the axis line of the optical fiber 12.

It is noted that the sheath may only have one of the shapes described above in cross-section which is perpendicular to the longitudinal direction thereof and including the light transmission sections, and the shape of the other portion not including the light transmission section does not necessarily have the same shape as the light transmission section.

An operation of the optical probe 10 formed in the aforementioned manner will now be described. A not shown light source of laser or the like is provided in the optical tomography processing unit 53 shown in FIG. 2, and light serving as measuring light L1 of the light outputted from the light source is guided through the optical fiber 69 and inputted to the optical fiber 12. The measuring light L1 is guided through the optical fiber 12 and outputted from the tip thereof, which is focused by the GRIN lens 14 and reflected by the prism mirror 15 so that the optical path thereof is deflected by 90 degrees, and outputted to the outside of the optical probe 10 through the light transmission section 16 of the sheath 11.

Then, when the shaft rotation motor 67 is driven, the flexible shaft 17 is rotated by the rotation of the gear wheels 66 and 65, thereby GRIN lens 14, prism mirror 15, and optical fiber 12 are also rotated around the longitudinal axis line.

The rotation of the prism mirror causes the measuring light L1 outputted therefrom to be deflected in the circumferential direction of the probe 10 and to scan a measuring object Sb in the direction shown by the arrow R in FIG. 2. The measuring light L1 is scatter reflected from the measuring object Sb and a portion of the reflection light propagates in the same path as the measuring light L1 in the opposite direction. That is, the portion of the reflection light passes through the light transmission section 16 of the probe 11, reflected by the prism mirror 15, inputted and focused by the GRIN lens 14, guided by the optical fibers 12 and 69, and conveyed to the optical tomography processing unit 53. In the optical tomography processing unit 53, the reflection light is branched from the optical path toward the optical probe 10 and detected by a not shown light detector. Then, based on the output of the light detector, a tomography image of the measuring object Sb is formed and displayed on the monitor 54.

Figure 8:
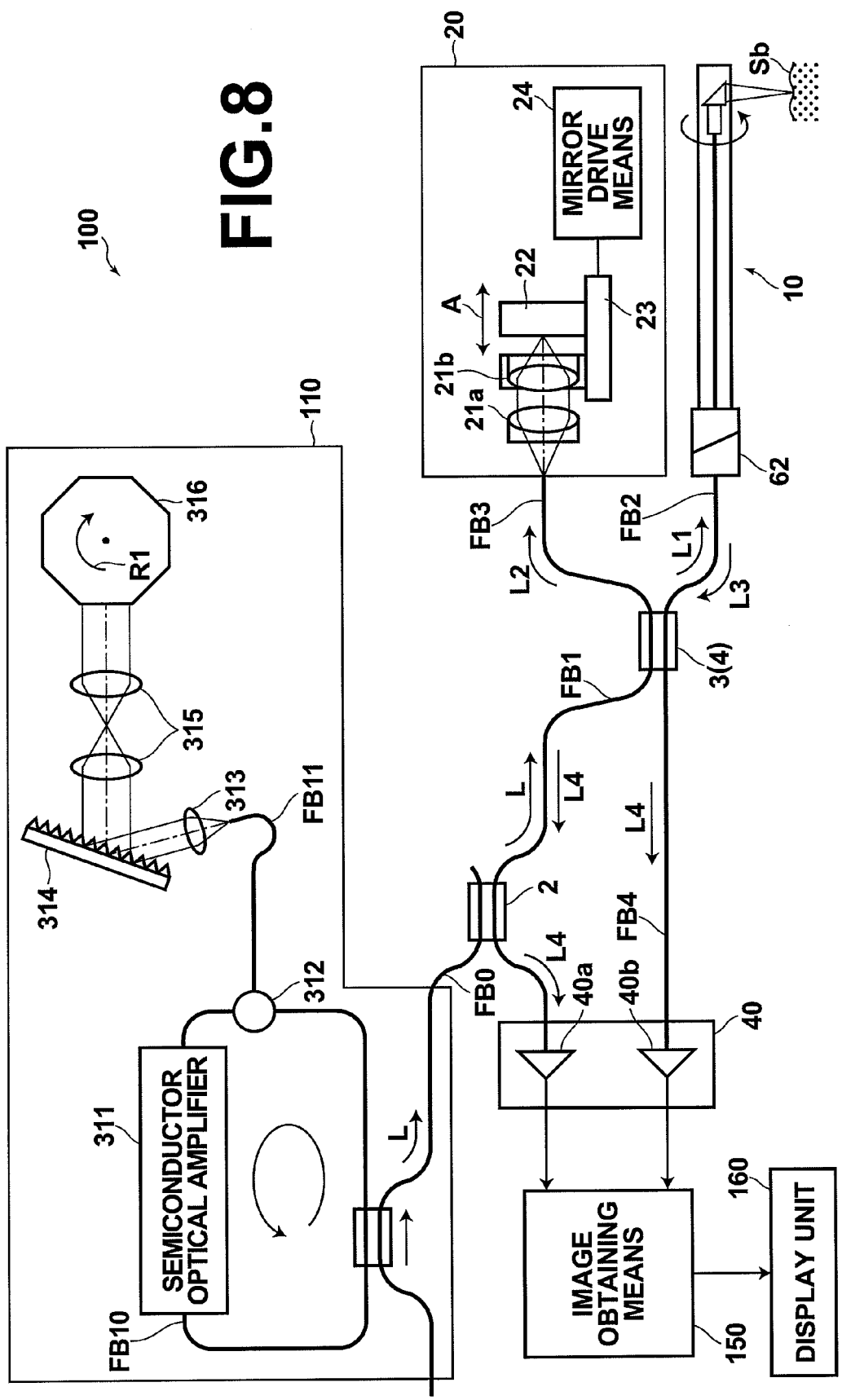
FIG. 8 is a schematic configuration diagram of an example SS-OCT measurement type optical tomography apparatus.

Next, an example optical tomography apparatus to which the optical probe is applied will be described. An optical tomography apparatus 100 shown in FIG. 8 is an apparatus for obtaining a tomography image of a biological measuring object, such as a living tissue, a cell, and the like in a body cavity by SS-OCT measurement. The optical tomography apparatus 100 includes: a light source unit 110 that outputs light L; a light splitting means 3 that splits the light L outputted from the light source unit 110 into measuring light L1 and reference light L2; an optical path length adjustment means 20 that adjusts the optical path length of the reference light L2 split by the light splitting means 3; the optical probe 10 that guides the measuring light L1 to the measuring object Sb; a light combining means 4 that combines reflection light L3 reflected from the measuring object Sb when the measuring light L1 is irradiated thereon with the reference light L2; an interference light detection means 40 that detects interference light L4 of the reflection light L3 and the reference light combined by the light combining means 4; and an image obtaining means 150 that detects intensities of the reflection light form a plurality of depth positions of the measuring object Sb based on the frequency and intensity of the interference light L4 detected by the interference light detection means 40, and obtains a tomography image of the measuring object Sb based on the intensity of the reflection light from each depth position.

The light source unit 110 of the present apparatus is a unit that outputs the laser light L while sweeping the wavelength thereof at a constant period. More specifically, the light source unit 110 includes a semiconductor amplifier (semiconductor gain medium) 311 and an optical fiber FB10, which is connected to each end of the semiconductor amplifier 311. The semiconductor amplifier 311 has functions to output a weak emission light to one end of the optical fiber FB10 when a drive current is injected and to amplify light inputted from the other end of the optical fiber FB10. When the drive current is supplied to the semiconductor amplifier 311, pulse laser light L is outputted to an optical fiber FB0 by the optical resonator formed of the semiconductor amplifier 311 and optical fiber FB10.

Further, a circulator 312 is connected to the optical fiber FB10, and a portion of light guided through the optical fiber FB10 is outputted to an optical fiber FB11 from the circulator 312. The light outputted from the optical fiber FB11 is passed through a collimator lens 313, a diffractive optical element 314, and an optical system 315, and then reflected by a rotational polygon mirror 316. The reflected light is inputted back to the optical fiber FB11 again through the optical system 315, diffractive optical element 314, and collimator lens 313.

Here, the rotational polygon mirror 316 is designed to rotate in the arrow R1 direction and the angle of each reflection surface is changed with respect to the optical axis of the optical system 315. This causes only the light having a wavelength in a particular wavelength range of the light dispersed by the diffractive optical element 314 to be returned to the optical fiber FB11. The wavelength of the light returned to the optical fiber FB11 is dependent on the angle between the optical axis of the optical system 315 and the reflection surface. The light having wavelengths within the particular wavelength range and inputted to the optical fiber FB11 is inputted back to the optical fiber FB10 from the circulator 312. As a result, laser light L having wavelengths within the particular wavelength range is outputted to the optical fiber FB0.

Accordingly, when the rotational polygon mirror 316 is rotated in the arrow R1 direction at a constant speed, the wavelength y of the light inputted back to the optical fiber FB11 will change with time at a constant period. In this way, the wavelength-swept laser light L is outputted from the light source unit 110 to the optical fiber FB0, which is passed through an optical fiber coupler 2 and inputted to an optical fiber FB1.

The light splitting means 3 is formed of, for example, a 2×2 optical fiber coupler, and splits the light L outputted from the light source unit 110 and guided through the optical fiber FB1 into the measuring light L1 and reference light L2. The light splitting means 3 is optically coupled to two optical fibers FB2 and FB3, and the measuring light L1 is guided through the optical fiber FB2, and the reference light L2 is guided through the optical fiber FB3. It is noted that the light splitting means 3 functions also as the light combining means 4.

The optical probe 10 shown in FIGS. 1A and 1B is optically coupled to the optical fiber FB2 and the measuring light L1 is guided from the optical fiber FB2 to the optical probe 10. The optical fiber FB2 includes the optical fiber 69 shown in FIG. 2 and coupled to the optical fiber 12 through the connector 62.

In the mean time, an optical path length adjustment means 20 is connected to the optical fiber FB3 on the output side of the reference light L2. The optical path length adjustment means 20 changes the optical path length of the reference light L2 in order to adjust the starting point of a tomography image acquisition, and includes a reflection mirror 22 that reflects the reference light L2 outputted from the optical fiber FB3, a first optical lens 21a disposed between the reflection mirror 22 and optical fiber FB3, and a second optical lens 21b disposed between the first optical lens 21a and reflection mirror 22.

The first optical lens 21a has functions to collimate the reference light L2 outputted from the core of the optical fiber FB3 and to focus the reference light L2 reflected by the reflection mirror 22 on the core of the optical fiber FB3. The second optical lens 21b has functions to focus the reference light L2 collimated by the first optical lens 21a on the reflection mirror 22 and to collimate the reference light L2 reflected by the reflection mirror 22.

Thus, the reference light L2 outputted from the optical fiber FB3 is collimated by the first optical lens 21a and focused on the reflection mirror 22 by the second optical lens 21b. Then, the reference light L2 reflected by the reflection mirror 22 is collimated by the second optical lens 21b and focused on the core of the optical fiber FB3 by the first optical lens 21a.

The optical path length adjustment means 20 further includes a base plate 23 on which the second optical lens and reflection mirror 22 are fixed, and a mirror moving means 24 that moves the base plate 23 in the optical axis directions of the first optical lens 21a. The optical path length of the reference light L2 is changed by moving the base plate 23 in the arrow A directions.

The light combining means 4 is formed of a 2×2 optical fiber coupler as described above, and combines the reference light L2 adjusted in the optical path length thereof by the optical path length adjustment means 20 with the reflection light L3 from the measuring object Sb, and the combined light is outputted to the interference light detection means 40 through an optical fiber FB4.

The interference light detection means 40 detects interference light L4 of the reflection light L3 and the reference light L2 combined by the light combining means 4. The interference light detection means 40 is connected to the image obtaining means 150 constituted by a computer system, such as a personal computer or the like, and the image obtaining means 150 is connected to a display unit 160 constituted by a CRT, a liquid crystal display, or the like. The display unit 160 may be the monitor 54 described earlier in relation to FIG. 2. The image obtaining means 150 detects the intensity of the reflection light L3 from each depth position of the measuring object Sb by performing Fourier transform on the interference light L4 detected by the interference light detection means 40 to obtain a tomography image of the measuring object Sb. Then, the obtained tomography image is displayed on the display unit 160. It is noted that the present example apparatus includes a mechanism in which interference light divided into halves by the light splitting means 3 is guided to light detectors 40a and 40b, and balanced detection is performed in a calculation means.

Here, detection of the interference light L4 by the interference detection means 40 and image generation by the image obtaining means 150 will be described briefly. For more detailed description, refer to the literature by Mitsuo Takeda, "Optical Frequency Scanning Interference Microscopes", Optics Engineering Contact, Vol. 41, No. 7, pp. 426-432, 2003.

When the measuring light L1 is irradiated on the measuring object Sb, reflection light L3 from the respective depths in the measuring object Sb interferes with the reference light L2 with various different optical path lengths. Now, assuming that light intensity of the interference pattern with respect to each optical path length difference "l" is S(l), then the light intensity I(k) detected by the interference light detection means 40 is expressed in the following.

$$I(k) = \int_0^\infty S(l)[1 + \cos(kl)]dl \quad (1)$$

where, "k" is the wave number, "l" is the optical path length difference. Formula (1) above can be regarded as an interferogram in optical frequency domain with the wave number k as a parameter. Accordingly, in the image obtaining means 150, the light intensity S(l) of the interference light L4 may be determined by performing a frequency analysis, through Fourier transform, on the interference light detected by the interference light detection means 40, thereby reflection information from each depth position may be obtained and an tomography image may be obtained. Then, the generated tomography image is displayed on the display unit 160.

Next, an operation of the optical tomography apparatus 100 constructed in the manner as described above will be described. First, the optical path length of the reference light L2 is adjusted by moving the base plate 23 in the arrow "A" direction in order to bring a measuring object Sb into a measurable range. Then, light L is outputted from a laser unit 10, and the light L is split into measuring light L1 and reference light L2 by the light splitting means 3. The measuring light L1 is guided by the optical probe 10 to a body cavity and irradiated on the measuring object Sb. Then, reflection light L3 from the measuring object Sb is combined with the reference light L2, reflected by the reflection mirror 22, by the light combining means 4. Then interference light L4 of the reflection light L3 and the reference light L2 is detected by the interference detection means 40. The signals of the detected interference light L4 are frequency analyzed in the image obtaining means 150, thereby a tomography image is obtained.

Thereafter, by scanning the measuring light L1 on the measuring object Sb by the optical probe 10 in the manner as described above, information of the measuring object Sb in the dept direction at each point along the scanning direction may be obtained, so that a tomography image of the cross-section that includes the scanning direction is obtained. The tomography image obtained in the manner as described above is displayed on the display unit 160. It is also possible, for example, to scan the measuring light L1 with respect to the measuring object Sb in a second direction which is orthogonal to the scanning direction described above by moving the optical probe 10 in the left-right directions in FIG. 8, thereby tomography images of the cross-sections that include the second direction may be obtained.

Figure 9:
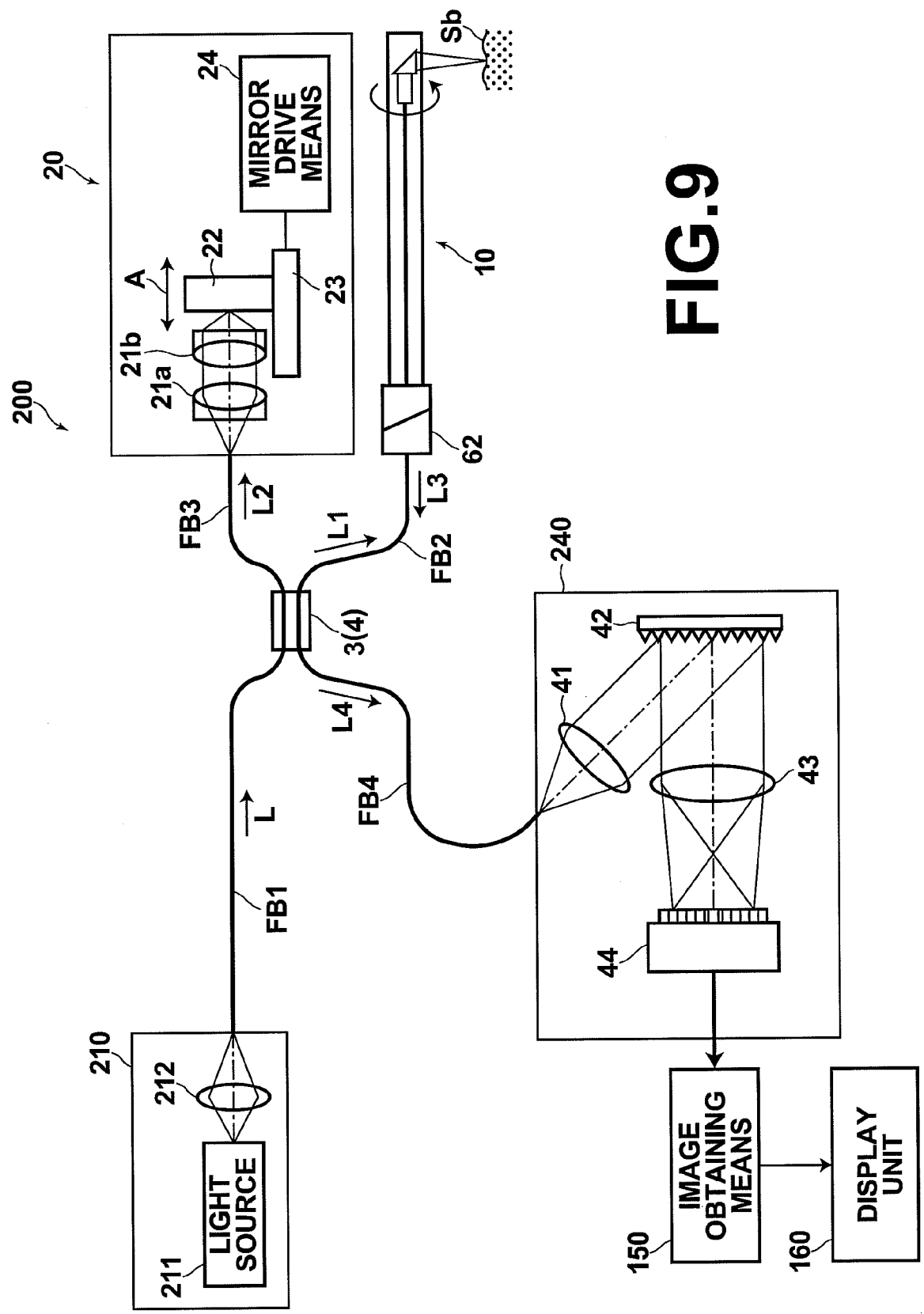
FIG. 9 is a schematic configuration diagram of an example SD-OCT measurement type optical tomography apparatus.

Next, another example optical tomography apparatus to which the optical probe of the present invention is applied will be described. A tomography apparatus 200 shown in FIG. 9 is an apparatus for obtaining a tomography image of a measuring object by the SD-OCT measurement described above. More specifically, the apparatus 200 differs from the optical tomography apparatus 100 shown in FIG. 8 in the structure of the light source unit and interference detection means. In the optical tomography apparatus 200 shown in FIG. 9, components identical to those of the optical tomography apparatus 100 shown in FIG. 8 are given the same reference symbols and will not be elaborated upon further here.

The light source unit 210 of the optical tomography apparatus 200 includes a light source 211 that emits low-coherence light, such as SLD (Super Luminescence Diode), ASE (Amplified Spontaneous Emission), or the like and an optical system 212 for inputting light emitted from the light source 211 to the optical fiber FB1. As for the light source 211, it is desirable that a light source capable of minimizing optical loss due to scattering and absorption of the light when passing through a measuring object is used and, for example, an ultrashort pulsed laser light source with wide spectral band is preferably used.

In the meantime, the interference detection means 240 is a means for detecting interference light L4 of the reflection light L3 and the reference light L2 combined by the light combining means 4. It includes a spectroscopic means 42 that separates the interface light L4 having a plurality of wavelength ranges into each wavelength range, and light detection means 44 provided for each wavelength range of the interference light L4 separated by the spectroscopic means 42. The spectroscopic means 42 is formed of, for example, a diffractive optical element or the like, and designed to separate the interference light L4 inputted from an optical fiber FB4 through a collimator lens 41 and outputs to the light detection means 44.

The light detection means 44 has, for example, a structure in which a plurality of optical sensors, such as CCDs or the like, is disposed one- or two-dimensionally, and the interference light L4 inputted through the optical lens 43 is detected by each of the sensors with respect to each of the wavelength ranges. Here, in the interference detection means 240, interference light L4 constituted by the spectrum of the light source unit 210 and a Fourier transformed function of the reflection information is observed. Then, the interference light L4 detected in the interference detection means 240 is frequency analyzed in the image obtaining means 150, thereby the reflection information from each depth position in the measuring object Sb is obtained and a tomography image is generated. The generated tomography image is displayed on the display unit 160.

In the optical tomography apparatus 200, the optical probe 10 having a structure identical to that used in the apparatus shown in FIG. 8 is also used, and the operation of the apparatus 200 is also identical to that of the apparatus 100 shown in FIG. 8.

So far, the optical tomography apparatuses 100 and 200 that use the optical probe 10 have been described. It will be appreciated that any of the optical probes according to the modified embodiments described above may be used instead of the optical probe 10.

Further, the SS-OCT and SD-OCT have been described as example optical tomography apparatuses to which the optical probe is applied. But the optical probe of the present invention may also be applied to a TD-OCT apparatus in the same way.

It is also noted that the structure of the optical probe is not limited to those described above, and may be modified in various ways. For example, the sheath covering the circumferential surface of the optical probe may be formed of a single part or a combination of a plurality of parts. A combination of a cap-like part constituting the tip of the optical probe and a sheath open at both ends may be used. Further, the sheath may be formed of two portions, a distal side having a light transmission section and a proximal side without the light transmission section, thereby allowing replacement of the distal side sheath.

Figure 10B:
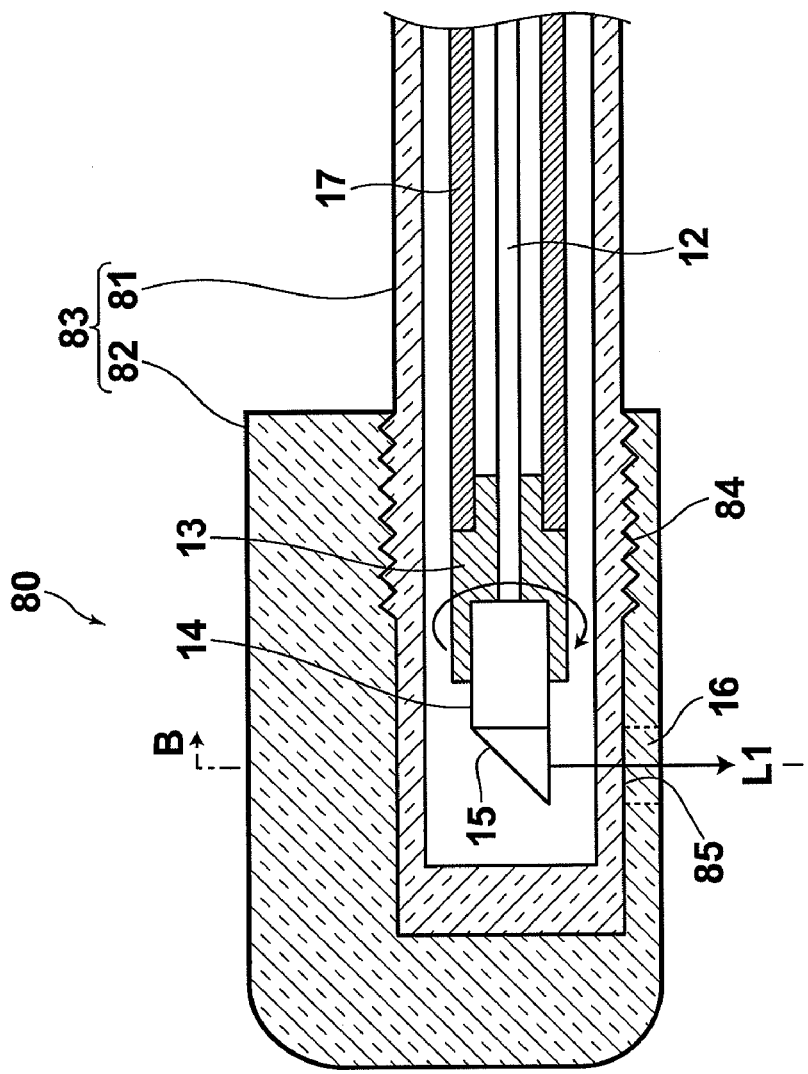
FIG. 10B is a schematic side cross-sectional view of an optical probe according to a second embodiment of the present invention.
Figure 10A:
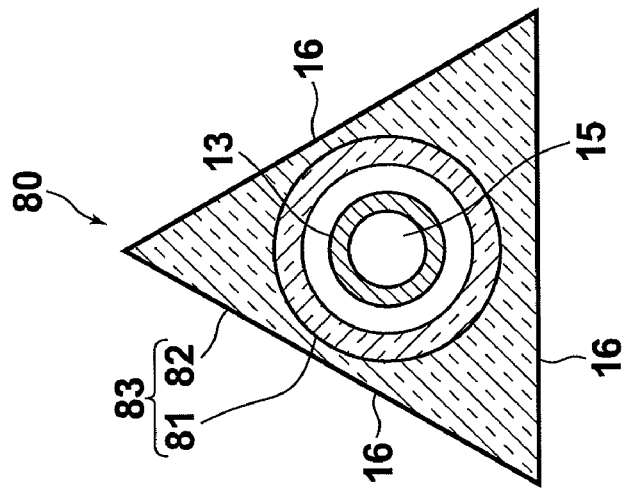
FIG. 10A is a cross-sectional view taken along the line B-B in FIG. 10B.

Hereinafter, example optical probes formed of a plurality of members will be described. First, the optical probed according to a second embodiment will be described with reference to FIGS. 10A and 10B. FIG. 10B is a side cross-sectional view of an optical probe 80 having a sheath 83 which includes a cylindrical sheath body 81, and a cap member 82 which is a cap-like member for covering the distal end section of the sheath body 81. FIG. 10A is a cross-sectional view taken along the line B-B in FIG. 10B.

The optical fiber 12, fixing member 13, GRIN lens 14, and prism mirror 15 are disposed in the internal space of the sheath body 81, as in the first embodiment.

The cap member 82 is removably attached to the sheath body 81 by a thread section 84 formed on the circumferential surface thereof. The cap member 82 may be formed, for example, in an angular tube such that the outer shape in cross-section which is perpendicular to the longitudinal direction of the optical probe 80 becomes an equilateral triangle shown in FIG. 10A. A light transmission section 16 for transmitting light deflected by the prism mirror 15 is formed, with its outer surface made flat, on each of the three side walls constituting the circumferential wall of the cap member 82. The light transmission section 16 is the portion between the two dashed lines in FIG. 10B.

Preferably, the cap member 82 and the sheath body 81 are made of the same material. For the material of the cap member 82 and the sheath body 81, for example, polytetrafluoroethylene (PTFE) resin polyethylene, polypropylene, or the like may be used. Where different materials are used for the cap member 82 and the sheath body 81, materials having a high optical transparency, a high flexibility, and the same or close values of refraction index with each other are desirable.

Preferably, a refraction index matching substance is filled in a gap 85 between the cap member 82 and the sheath body 81 on the optical path of the light deflected by the prism mirror 15 in order to reduce optical loss. If the gap 85 is very small, it is desirable that the inner surface of the cap member 82 or the outer surface of the sheath body 81 is coated with a refraction index matching substance. As for the refraction index matching substance, for example, a gel substance having a refraction index which is the same or close to that of the cap member 82 and the sheath body 81 may be used.

Figure 11:
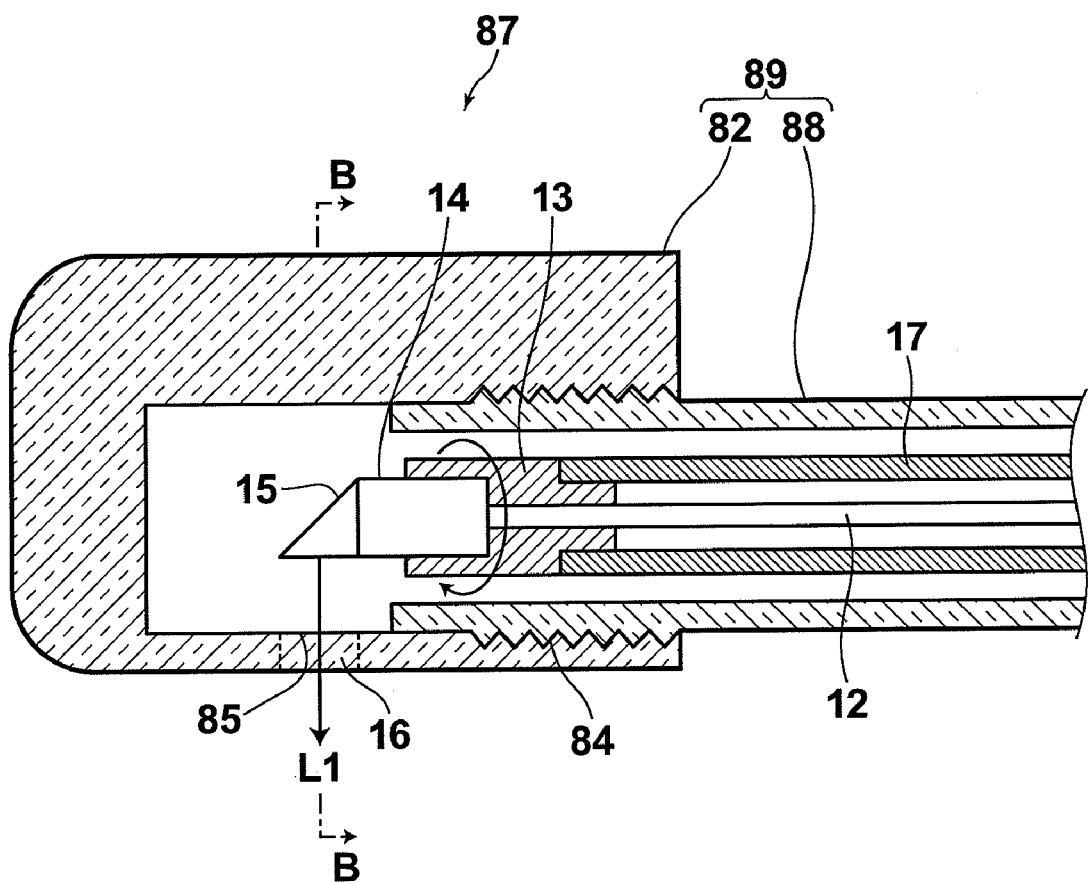
FIG. 11 is a side cross-sectional view of a modification of the optical probe of the present invention.

In the example shown in FIG. 10B, the sheath body 81 is structured such that it is closed at the tip, and to pass the deflected light therethrough. But, as the optical probe 87 shown in FIG. 11, it is also possible to form the sheath 89 using the cylindrical sheath body 88 which is open at the tip, instead of the sheath body 81 shown in FIG. 10B. The sheath body 88 shown in FIG. 11 is formed shorter in the distal end than the sheath body 81 in order not to cover the prism mirror 15. In the optical probe 80, the deflected light needs to pass through the sheath body 81 and the cap member 82, whereas in the optical probe 87, the deflected light needs to pass through only the cap member 82, so that it may reduce more optical loss than the optical probe 80.

Next, the optical probe according to a third embodiment will be described with reference to FIGS. 12A and 12B. FIG. 12B is a side cross-sectional view of an optical probe 90 having a sheath 93 which includes a cylindrical sheath body 91, and a strip-like member 92. FIG. 12A is a cross-sectional view taken along the line C-C in FIG. 12B.

The optical fiber 12, fixing member 13, GRIN lens 14, and prism mirror 15 are disposed in the internal space of the sheath body 81, as in the first embodiment.

The strip-like member 92 is removably attached to the sheath body 91 by a click section 94. The click section 94 shown in FIG. 12B includes a protrusion provided on the sheath body 91 and a groove provided on the strip-like member 92 such that it engages with the protrusion.

The strip-like member 92 may be formed, for example, in an angular tube such that the outer shape in cross-section which is perpendicular to the longitudinal direction of the optical probe 90 becomes an equilateral triangle shown in FIG. 12A. A light transmission section 16 for transmitting light deflected by the prism mirror 15 is formed, with its outer surface made flat, on each of the three side walls constituting the circumferential wall of the strip-like member 92. The light transmission section 16 is the portion between the two dashed lines in FIG. 12B.

As for the material of the strip-like member, materials identical to those of the cap member in the second embodiment may be used. In the present embodiment, it is preferable that a refraction index matching substance is filled between the strip-like member 92 and the sheath body 91, or coating them with a refraction index matching substance in order to reduce optical loss, as in the second embodiment.

In the second or third embodiment, the description has been made of a case in which a plurality of members constituting the sheath is structured to be removably attachable and an engagement section of a thread section or a click section is introduced. But the structure is not limited to those described, and an engagement section of different configuration may also be used.

Alternatively, when forming the sheath with a plurality of members, they are not necessarily made removably attachable, and they may be fixed together by adhesive. In this case, it is preferable that an adhesive having a refraction index which is the same or close to that of the members constituting the sheath.

Figure 14:
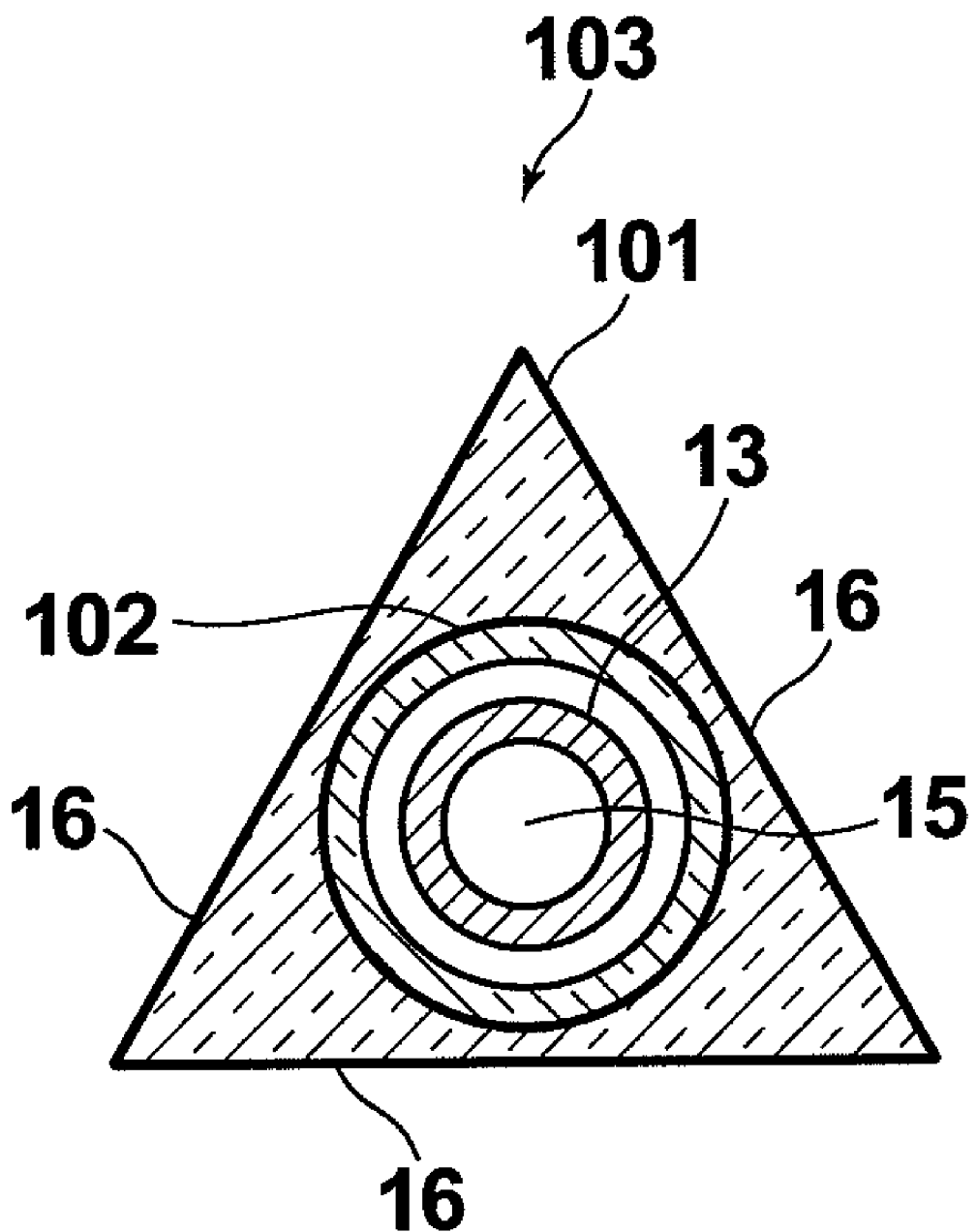
FIG. 14 is a cross-sectional view taken along the line D-D in FIG. 13B.

Next, the optical probe according to a fourth embodiment will be described with reference to FIGS. 13A, 13B and 14. FIGS. 13A and 13B are side cross-sectional views of the distal end side of the optical probe 103 in the insertion section of an endoscope. FIG. 14 is a cross-sectional view taken along the line D-D in FIG. 13B. The optical probe 103 in the present embodiment has a characteristic feature in which a cover member 101 is provided within a forceps channel 64 of the insertion section of the endoscope in advance, and the cover member 101 is mounted on a sheath body 102 when used.

As shown in FIG. 13A, in the present embodiment, an enlarged diameter section 64c having a larger inner diameter than the proximal end side is formed at the distal end section of the forceps channel 64, and the cover member 101 is storably disposed inside the enlarged diameter section 64c. The cover member 101 is slidable along the inner wall of the enlarged diameter section 64c, and the movable range thereof is limited by stepping sections 64d and 64e provided on the enlarged diameter section 64c.

The cover member 101 may be formed, for example, in an angular tube such that the outer shape in cross-section which is perpendicular to the longitudinal direction of the optical probe 103 becomes an equilateral triangle shown in FIG. 14. A light transmission section 16 for transmitting light deflected by the prism mirror 15 is formed, with its outer surface made flat, on each of the three side walls constituting the circumferential wall of the cover member 101. The light transmission section 16 is the portion between the two dashed lines in FIG. 13B.

A step section 101a which is enlarged in diameter is formed at the circumferential rear end of the cover member 101, and when the cover member 101 is stored in the enlarged diameter section 64c, the step section 101a is abutted to the step section 64e. In the mean time, the tip of the forceps channel 64 is formed smaller in inner diameter than the enlarged diameter section 64c by forming the step section 64d, and the step section 101a of the cover member 101 has a sufficient size to abut to the step section 64d.

Further, the cover member 101 has substantially an angular tube shape with an inner diameter that allows insertion of the distal end section of the cylindrical sheath body 102, but a step section 101b is formed on the inner surface thereof at the distal end side so that the diameter of the tip opening section becomes smaller than the diameter of the sheath body 102.

The optical fiber 12, fixing member 13, GRIN lens 14, and prism mirror 15 are disposed in the internal space of the sheath body 102, as in the first embodiment. In the present embodiment, the cover member 101 and the sheath body 102 constitute a sheath, and the sheath and the optical fiber 12 and the like disposed in the sheath body 102 constitute the optical probe 103.

An operation in the present embodiment will be described. Initially, the insertion section 55 is inserted into a body cavity with the cover member 101 being stored in the enlarged diameter section 64c. After insertion of the insertion section 55 is completed, the sheath body 102 is inserted into the forceps channel 64 and moved in the tip direction thereof. Then, the sheath body 102 is inserted into inside of the cover member 101, as shown in FIG. 13A.

When the sheath body 102 is further moved from the state shown in FIG. 13A in the tip direction, the tip of the sheath body 102 abuts to the step section 101b of the cover member 101 and the cover member 101 is mounted on the sheath body 102.

From this state, when the sheath body 102 is further moved in the tip direction, the cover member 101 is pushed by the tip of the sheath body 102 and the cover member 101 is mounted on the sheath body 102. Then, the integrated optical probe 103 protrudes from the insertion section 55 and further moves in the tip direction. The movement of the optical probe 103 continues until the step section 101a at the rear end of the cover member 101 abuts to the step section 64d of the enlarged diameter section 64c, and the movement is stopped by this abutment.

In the cover member 101 shown in FIG. 13B, the position of each light transmission section 16 is predetermined such that when the sheath body 102 is covered by the cover member 101, the light deflected by the prism mirror 15 is outputted through the light transmission section 16.

The structure of the cover member 101 is not limited to that shown in FIGS. 13A and 13B. For example, as shown in FIG. 15, an optical probe 105 may also be constructed using a cap-like cover member 104 which is closed at the tip, instead of using the cover member 101 shown in FIGS. 13A and 13B.

The use of the cover member 104 shown in FIG. 15 allows the tip of the forceps channel 64 to be airtight, which prevent the sheath body 102 is prevented from touching the measuring object, bodily fluid, or the like. This may prevent the sheath body 102 from being contaminated, resulting in ease of the maintenance. In this case, however, a forceps can not be used by inserting through the forceps channel 64 while the cover member 104 is installed therein. It is desirable, therefore, that the cover member 104 is installed in a tube different from the forceps channel.

If the sheath is formed of a plurality of members and made removably attachable as described in the second to fourth embodiments, cleaning of the members and replacement of a deteriorated member become easy. The ease of replacement allows provision of a plurality of types of cap sections or band sections having different outer shapes or the like, and selection and use of one of them appropriate for the measurement. Further, if only a portion of the sheath having a light transmission section is formed in a particular shape, such as a polygon in outer shape or the like, while the sheath body which constitutes the most part of the sheath is formed in cylindrical, the manufacturing becomes easy in comparison with a sheath formed of a single part and having a polygonal shape or the like in outer shape over the entire length, and the productivity is improved.

Further, the fourth embodiment may also provide the following advantageous effects. In the first to third embodiments, the forceps channel to which the optical probe is inserted needs to have a diameter which corresponds to the diameter of the portion of the optical probe having a light transmission section of the present invention over the entire insertion path, which may possibly result in a larger diameter of the forceps channel over the entire length. In contrast, in the fourth embodiment, the forceps channel needs to have a large diameter only in the portion where the cover member 101 is slid, and the rest of the portion constituting the most part of the forceps channel may have a smaller diameter that allows insertion of the cylindrical sheath body 102, so that the problem of the large diameter concerned in the first to third embodiments may be avoided.

In the second to fourth embodiments, a sheath having a triangular outer shape in cross-section having the light transmission sections is described as an example, but the shape is not limited to this. Even when the sheath is formed of a plurality of members, the outer shape of the removably attachable member having the light transmission sections may be formed in a polygon, a polygon with rounded corners, or substantially an ellipsoid.

Figure 16A:
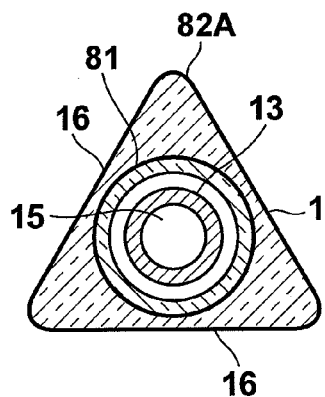
FIGS. 16A to 16E illustrate cross-sectional shapes of modifications of the optical probe of the present invention.
Figure 16B:
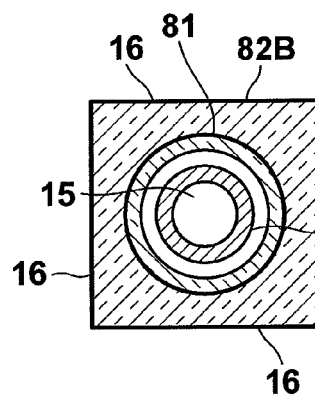
Figure 16C:
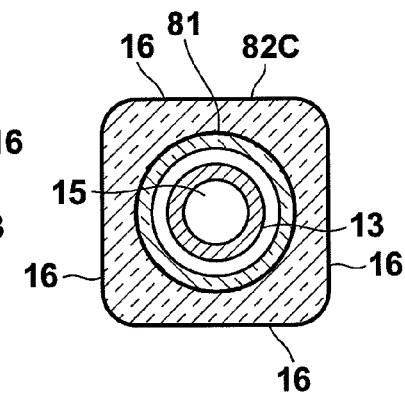
Figure 16D:
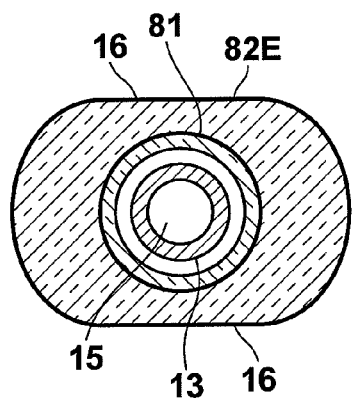
Figure 16E:
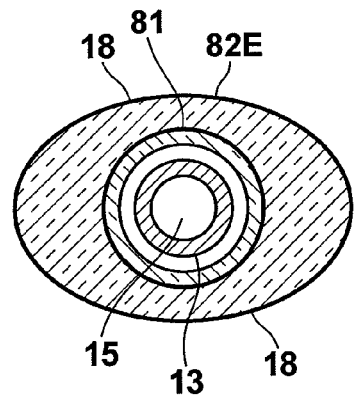

Such examples are shown in cross-section in FIGS. 16A to 16E. FIG. 16A shows a cap member 82A having an outer shape of equilateral triangle with rounded corners. FIG. 16B shows a cap member 82B having an outer shape of square. FIG. 16C shows a cap member 82C having an outer shape of square with rounded corners. FIG. 16D shows a cap member 82D having an outer shape formed of opposite two planar surfaces connected by curved surfaces. Modifications identical to those of the cap member shown above may be made also to the strip-like member in the third embodiment and the cover member in the fourth embodiment.

Further, optical probes described in the second to fourth embodiment may be applied to an optical tomography apparatus in the same manner as the optical probe in the first embodiment.

What is claimed is:

1. An elongated optical probe to be inserted into a tube which is open at a distal end portion of an insertion section of an endoscope, the probe comprising:
   a sheath constituting an outer circumferential surface of the optical probe and having a cross section taken perpendicular to the longitudinal direction having a shape that is a triangle and having three side walls;
   an optical fiber laid in an internal space of the sheath along a longitudinal direction thereof;
   a deflection scanning means disposed in the internal space of the sheath to deflect light outputted from the optical fiber, and rotatable around an axis line extending in the longitudinal direction to scan the deflected light in a circumferential direction of the axis line; and
   a plurality of light transmission sections for transmitting the scanning light, each provided on one of the three side walls of the sheath along the circumferential direction and each having an outer surface that is flat.

2. An elongated optical probe to be inserted into a tube which is open at a distal end portion of an insertion section of an endoscope, the probe comprising:
   a sheath constituting an outer circumferential surface of the optical probe;
   an optical fiber laid in an internal space of the sheath along a longitudinal direction thereof;
   a deflection scanning means disposed in the internal space of the sheath to deflect light outputted from the optical fiber, and rotatable around an axis line extending in the longitudinal direction to scan the deflected light in a circumferential direction of the axis line;
   a plurality of light transmission sections for transmitting the scanning light, each provided on a side wall of the sheath along the circumferential direction and each having an outer surface that is flat;
   wherein the inner shape of the sheath in cross-section which is perpendicular to the longitudinal direction and including the light transmission sections is a circle with respect to a point on the axis line.

3. An elongated optical probe to be inserted into a tube which is open at a distal end portion of an insertion section of an endoscope, the probe comprising:
   a sheath constituting an outer circumferential surface of the optical probe;
   an optical fiber laid in an internal space of the sheath along a longitudinal direction thereof;
   a deflection scanning means disposed in the internal space of the sheath to deflect light outputted from the optical fiber, and rotatable around an axis line extending in the longitudinal direction to scan the deflected light in a circumferential direction of the axis line;
   a plurality of light transmission sections for transmitting the scanning light, each provided on a side wall of the sheath along the circumferential direction and each having an outer surface that is flat;
   wherein the sheath comprises a first member having a cylindrical shape and a second member which is removably attachable to the first member and on which the plurality of light transmission sections is provided along the circumferential direction.

4. The optical probe according to claim 3, wherein the second member is a cap member that covers a distal end portion of the first member.

5. The optical probe according to claim 3, wherein the second member is a strip-like member that covers a portion of the circumferential surface of the first member.

6. The optical probe according to claim 3, wherein:
   the second member is a cover member having an inner diameter that allows insertion of a distal end portion of the first member and stored inside of the tube of the insertion section of the endoscope, the cover member being slidable in the longitudinal direction of the tube; and
   the sheath is configured such that the cover member protrudes from the insertion section while covering the distal end portion of the first member when the first member is moved in the tip direction of the tube and allows the light to be outputted through one of the light transmission sections.

7. An elongated optical probe to be inserted into a tube which is open at a distal end portion of an insertion section of an endoscope, the probe comprising:
   a sheath constituting an outer circumferential surface of the optical probe;
   an optical fiber laid in an internal space of the sheath along a longitudinal direction thereof;
   a deflection scanning means disposed in the internal space of the sheath to deflect light outputted from the optical fiber, and rotatable around an axis line extending in the longitudinal direction to scan the deflected light in a circumferential direction of the axis line; and a plurality of light transmission sections provided on a side wall of the sheath along the circumferential direction to transmit the scanning light, wherein the outer shape of a cross-section of the sheath taken perpendicular to the longitudinal direction and including the light transmission sections is substantially a noncircular ellipse, and wherein the inner shape of the sheath in cross-section which is perpendicular to the longitudinal direction and including the light transmission sections is a circle with respect to a point on the axis line.

8. An elongated optical probe to be inserted into a tube which is open at a distal end portion of an insertion section of an endoscope, the probe comprising:

a sheath constituting an outer circumferential surface of the optical probe;

an optical fiber laid in an internal space of the sheath along a longitudinal direction thereof;

a deflection scanning means disposed in the internal space of the sheath to deflect light outputted from the optical fiber, and rotatable around an axis line extending in the longitudinal direction to scan the deflected light in a circumferential direction of the axis line; and a plurality of light transmission sections provided on a side wall of the sheath along the circumferential direction to transmit the scanning light, wherein the outer shape of a cross-section of the sheath taken perpendicular to the longitudinal direction and including the light transmission sections is substantially a noncircular ellipse, and wherein the sheath comprises a first member having a cylindrical shape and a second member which is removably attachable to the first member and on which the plurality of light transmission sections is provided along the circumferential direction.

9. The optical probe according to claim 8, wherein the second member is a cap member that covers a distal end portion of the first member.

10. The optical probe according to claim 8, wherein the second member is a strip-like member that covers a portion of the circumferential surface of the first member.

11. The optical probe according to claim 8, wherein:

the second member is a cover member having an inner diameter that allows insertion of a distal end portion of the first member and stored inside of the tube of the insertion section of the endoscope, the cover member being slidable in the longitudinal direction of the tube; and the sheath is configured such that the cover member protrudes from the insertion section while covering the distal end portion of the first member when the first member is moved in the tip direction of the tube and allows the light to be outputted through one of the light transmission sections.

12. An optical tomography apparatus, comprising:

a light source that emits light;

a light splitting means that splits light emitted from the light source into measuring light and reference light;

an irradiation optical system that irradiates the measuring light on a measuring object;

a light combining means that combines reflection light from the measuring object when the measuring light is irradiated thereon with the reference light;

an interference light detection means that detects interference light of the combined reflection and reference light; and an image obtaining means that detects an intensity of reflection light from each of a plurality of depth positions of the measuring object based on the frequency and intensity of the detected interference light, and obtains a tomography image of the measuring object based on the intensity of the reflection light from each of the depth positions, wherein the irradiation optical system includes an elongated optical probe to be inserted into a tube which is open at a distal end portion of an insertion section of an endoscope, the optical probe including:

a sheath constituting an outer circumferential surface of the optical probe and having a cross section taken perpendicular to the longitudinal direction having a shape that is a triangle and having three side walls;

an optical fiber laid in an internal space of the sheath along a longitudinal direction thereof;

a deflection scanning means disposed in the internal space of the sheath to deflect light outputted from the optical fiber, and rotatable around an axis line extending in the longitudinal direction to scan the deflected light in a circumferential direction of the axis line; and a plurality of light transmission sections for transmitting the scanning light, each provided on one of the three side walls of the sheath along the circumferential direction and each having an outer surface that is flat.

* * * * *